United States Patent
Yen (12)

(10) Patent No.: US 6,264,988 B1
(45) Date of Patent: *Jul. 24, 2001

(54) FIBRINOGEN-COATED MICROSPHERES

(75) Inventor: Richard C. K. Yen, Yorba Linda, CA (US)

(73) Assignee: Hemosphere, Inc., Yorba Linda, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/090,557

(22) Filed: Jun. 4, 1998

Related U.S. Application Data

(60) Provisional application No. 60/048,685, filed on Jun. 5, 1997.

(51) Int. Cl.[7] ............................................ A61K 9/16
(52) U.S. Cl. ...................... 424/490; 424/489; 424/491; 424/494; 514/2; 514/12; 514/834; 530/382
(58) Field of Search ................................. 424/489, 490, 424/491, 494; 514/2, 12, 834; 530/382

(56) References Cited

U.S. PATENT DOCUMENTS

| 3,565,559 | 2/1971 | Sato et al. ............................. 424/37 |
| 3,663,685 | 5/1972 | Evans et al. ............................ 424/1 |

(List continued on next page.)

FOREIGN PATENT DOCUMENTS

| WO 91/12823 | 9/1991 | (WO) . |
| WO 94/08627 | 4/1994 | (WO) . |
| WO 96/18388 | 6/1996 | (WO) . |
| WO 96/39128 | 12/1996 | (WO) ............................. A61K/9/64 |
| WO 96/40075 | 12/1996 | (WO) ............................. A61K/9/16 |
| WO 97/10850 | 3/1997 | (WO) . |
| WO 97/44015 | 11/1997 | (WO) ............................. A61K/9/16 |
| WO 98/17319 | 4/1998 | (WO) ............................ A61K/47/48 |

OTHER PUBLICATIONS

Agam et al., "Erythrocytes with covalently bound fibrinogen as a cellular replacement for the treatment of thrombocytopenia", *Euro. J. Clin. Invest.* 22:105 (1992).

Beer et al., "Immobilized Arg–Gly–Asp (RGD) Peptides of Varying Lengths as Structural Probes of the Platelet Glycoprotein IIb/IIIa Receptor", *Blood* 79:117 (1992).

Coller et al., "Thromboerythrocytes In Vitro Studies of a Potential Autologous, Semi–artificial Alternative to Platelet Transfusions", *J. Clin. Invest.* 89:546 (1992).

Levi et al., "Fibrinogen–coated albumin microcapsules reduce bleeding in severely thrombocytopenic rabbits," *Nature Medicine* 5:1 107–111 (Jan. 1999).

Pytela et al., "Platelet membrane glycoprotein IIb/IIa:a member of a family of Arg–Gly–Asp specific adhesion receptor." *Science* 231:1559–1562 (Mar. 28, 1986).

(List continued on next page.)

Primary Examiner—Thurman K. Page
Assistant Examiner—Lakshmi Channavajjala
(74) Attorney, Agent, or Firm—Townsend & Townsend & Crew

(57) ABSTRACT

The invention provides compositions comprising microspheres of fibrinogen-coated cross-linked albumin microspheres having a size range of primarily from about 100 to about 5000 nanometers diameter, wherein the composition is substantially free microspheres and microsphere aggregates having a diameter of more than 10 micrometers. At least a portion of the fibrinogen on the surface of the microspheres is covalently attached. The particles of the invention are useful for reducing bleeding time when administered to a human or other animal.

21 Claims, 22 Drawing Sheets

U.S. PATENT DOCUMENTS

| | | | |
|---|---|---|---|
| 3,663,686 | 5/1972 | Grotenhuis et al. | 424/1 |
| 4,107,288 | 8/1978 | Oppenheim | 424/22 |
| 4,147,767 | 4/1979 | Yapel, Jr. | 424/22 |
| 4,269,821 | 5/1981 | Kreuter et al. | 424/19 |
| 4,325,937 | 4/1982 | Spence et al. | 424/16 |
| 4,410,507 | 10/1983 | Chia et al. | 424/1.1 |
| 4,818,542 | 4/1989 | Deluca et al. | 424/491 |
| 4,822,535 | 4/1989 | Ekman et al. | 264/4.3 |
| 4,921,705 | 5/1990 | Arai et al. | 424/450 |
| 4,963,367 | 10/1990 | Ecanow | 424/485 |
| 5,049,322 | 9/1991 | Devissaguet et al. | 264/4.1 |
| 5,069,936 * | 12/1991 | Yen | 427/213.33 |
| 5,104,674 | 4/1992 | Chen et al. | 424/573 |
| 5,149,540 | 9/1992 | Kunihiro et al. | 424/489 |
| 5,308,620 | 5/1994 | Yen | 424/484 |
| 5,374,441 | 12/1994 | Gibson et al. | 426/656 |
| 5,518,709 | 5/1996 | Sutton et al. | 424/9.52 |
| 5,616,311 * | 4/1997 | Yen | 424/1.33 |
| 5,691,160 | 11/1997 | Janmey et al. | 435/13 |
| 5,716,643 * | 2/1998 | Yen | 424/491 |
| 5,725,804 | 3/1998 | Yen | 252/314 |
| 5,741,478 | 4/1998 | Osborne et al. | 424/9.52 |
| 5,955,108 | 9/1999 | Sutton et al. | 424/489 |
| 5,977,313 | 11/1999 | Heath et al. | 530/382 |

OTHER PUBLICATIONS

Vickers, "DP–stimulated fibrinogen binding is neessary for some of the inositol phospholipid changes found in ADP––stimulated platelets." *European Journal of Biochemistry* 216:231–237 (1993).

Widder et al., "Magnetically Responsive Microspheres and Other Carriers For the Biophysical Targeting of Antitumor Agents", *Adv. Pharmacol. and Chemother.* 16:213–271 (1979).

* cited by examiner

FIBRINOGEN-COATED MICROSPHERES

This application claims the benefit of U.S. Provisional Application No. 60/048,685, filed Jun. 5, 1997, the disclosure of which is incorporated by reference.

BACKGROUND OF THE INVENTION

Platelets play a critical role in hemostasis. A deficiency of platelets (thrombocytopenia) or dysfunction of platelets present at normal levels results in longer-than-normal bleeding time and other disorders. Thrombocytopenia is currently treated with platelet concentrates obtained from healthy donors (Rintels el al., 1994, *Transfusion Med.* 8:1131). Such treatment has severe drawbacks, however, including (i) the potential transmission of infectious agents, including bacterial and viral agents, (ii) the short shelf-life of donor platelets and the requirement for specialized equipment and methods for handling and storage of platelets, and (iii) a high incidence of alloimmunization. There is, therefore, an urgent need for a platelet substitute that is both efficacious and safe and can be given to patients of different blood types without major transfusion incompatibility.

Physicians and scientists have long sought a source of artificial platelets. As one example, investigators have attached fibrinogen to erythrocytes (Agam et al., 1992, *Euro J Clin Invest* 22:105; Beer et al., 1992, *Blood* 79:117; Collar et al., 1992, *J Clin. Invest.* 89:546). However, the erythrocyte-based system suffers from i) the difficulty of attaching fibrinogen to large numbers of erythrocytes, ii) the requirement for cross-matching with patients, iii) the inherent short storage life and instability of the treated erythrocytes, iv) the potential of transmission of infectious agents.

Other approaches to replace the need of platelet infusions involve the use of lyophilized human platelets, fibrinogen attached to platelet membrane microvesicles, and other attempts at making artificial platelets. However, these products typically have a short in vivo half life or are not efficacious in vivo.

There is, therefore, a need for a platelet substitute that is convenient and effective.

BRIEF DESCRIPTION OF THE INVENTION

In one aspect the invention relates to a suspension of particles of cross-linked albumin, which are monodisperse in the suspension, and have a size range of primarily from about 50 to about 5000 nanometers diameter. The particles have fibrinogen on the surface of the particle, at least some of which is covalently attached. The suspension is substantially free of large particles and aggregates of particles.

In preferred embodiments the particles comprise human serum albumin cross-linked with a polyaldehyde, such as glutaraldehyde, and human fibrinogen covalently attached by a polyaldehyde, such as glutaraldehyde. In a preferred embodiment the particles have at least about $4 \times 10^{12}$ molecules of fibrinogen per $10^9$ particles.

In a preferred embodiment the particles have a sponge-like internal structure with fenestrations on the surface leading to internal matrices. Fibrinogen may be disposed within the internal matrices or cavities.

Particles of the invention may be suspended in a liquid, e.g., an aqueous suspension. Alternatively the suspension may be dried (e.g., lyophilized) to form a powder. Thus the invention also provides a composition comprising a plurality of particles that, upon addition of a liquid such as water or normal saline, forms a suspension of cross-linked albumin particles with a size range of primarily from about 50 to about 5000 nanometers diameter and fibrinogen on the surface, which suspension is substantially free of large particles and aggregates of particles.

In preferred embodiments the composition of the invention, whether as a liquid suspension of particles or a dry powder of particles, includes an excipient.

In another aspect, the invention provides a method of making a composition useful for reducing bleeding time in an animal by the steps of: adding a desolvating agent to an aqueous mixture of a protein and a surfactant, whereupon a turbid mixture comprising substantially monodisperse protein microspheres results; adding a first crosslinking agent to the turbid mixture; removing large particles and aggregates from the mixture; adding a second cross-linking agent, which may be the same as the first cross-linking agent; and adding fibrinogen. In a preferred embodiment the removal of large particles and aggregates is by filtration. In another preferred embodiment the removal of large particles and aggregates is by centrifugation.

In an alternative aspect, the invention provides a method of making a composition by the steps of: adding a desolvating agent to an aqueous mixture of a protein and a surfactant, whereupon a turbid mixture comprising substantially monodisperse protein microspheres; adding a crosslinking agent to the turbid mixture; adding fibrinogen to the mixture whereupon the particles are coated with the fibrinogen; and removing large particles and aggregates from the mixture.

In yet another aspect, the invention provides a method of reducing bleeding time in an animal comprising administering a therapeutically effective amount of the compositions of the invention, for example in the treatment of thrombocytopenia.

BRIEF DESCRIPTION OF THE FIGURES

FIG. 11A shows a TS1 reconstituted suspension; FIG. 11B–E show the bulk suspension before Membrex filtration (FIG. 11B); retentate of the Membrex system (FIG. 11C); filtrate from the Membrex filter before diafiltration (FIG. 11D); and liquid suspension of the same filtrate after diafiltration in the Asahi cartridge (FIG. 11E); FIG. 11F shows TS3 prior to Membrex filtration; FIG. 11G shows TS3 after Membrex filtration, diafiltration with the Asahi apparatus, lyophilization, and reconstitution with normal saline; FIG. 11H shows a TS3 reconstituted suspension.

FIG. 12A shows reconstituted suspensions of TS1 and TS3; FIG. 12B shows the amplified distribution of the spheres with average diameter of 0.8 micron; FIG. 12C shows the concentration of the 0.8 micron spheres as a percentage of the entire sphere population; FIG. 12D shows that TS1 had a population of sphere about 4 micron in diameter, which was essentially absent in TS3.

FIG. 15A shows a cross section of a CS; FIG. 15B shows a cross section of unstained TS1; FIG. 15C shows TS1 stained with a uranyl acetate/lead citrate solution; FIG. 15D shows TS1 treated with buffer and protein A-gold in the absence of anti-human fibrinogen IgG; FIG. 15E shows the cross section of TS1 labeled with sheep anti-human fibrinogen IgG tagged with protein A-gold.

FIG. 17 shows the FPA content of TS1.

DETAILED DESCRIPTION OF THE INVENTION

Terminology

Figure 1:
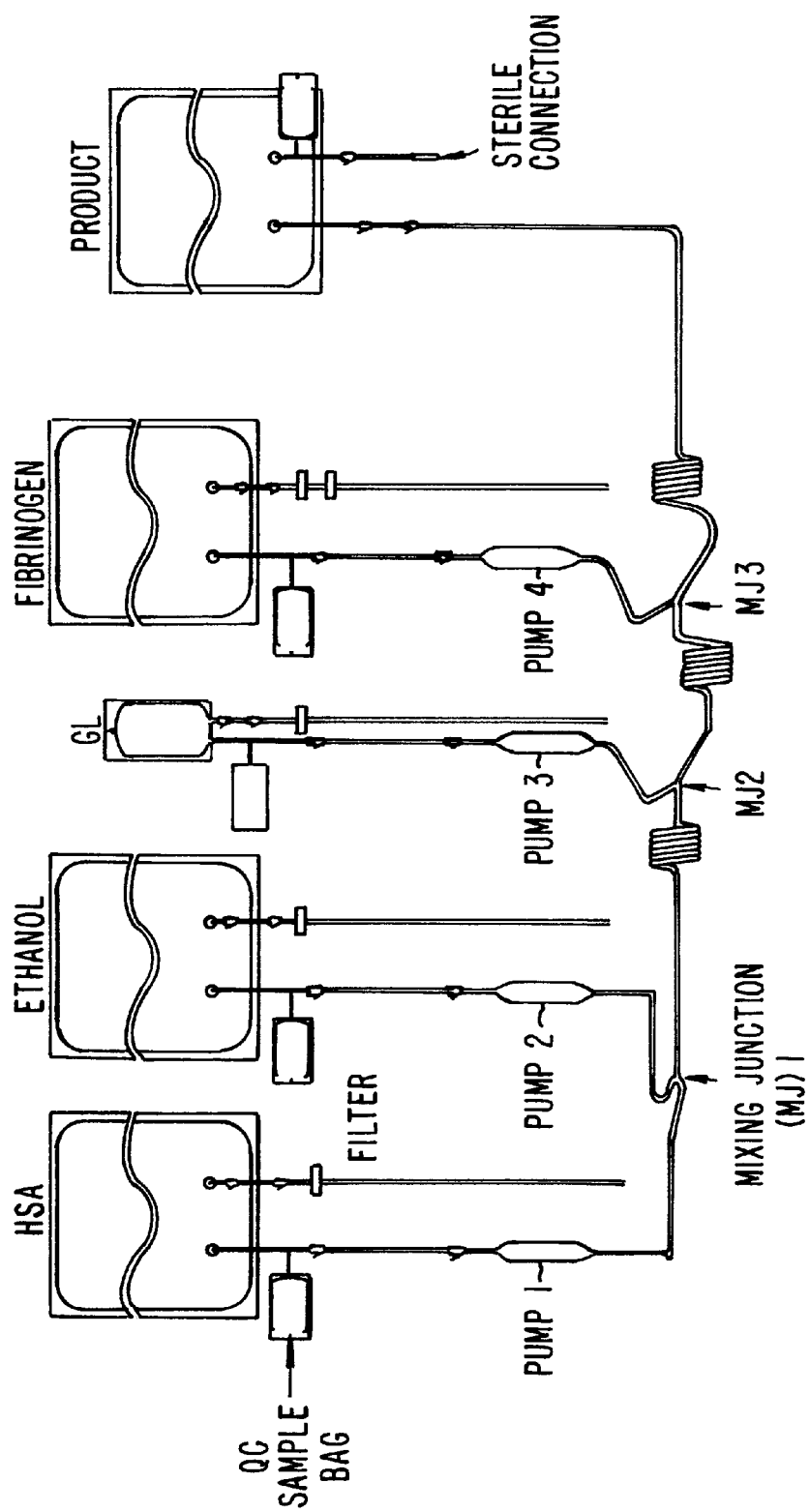
FIG. 1 shows an apparatus for continuous production of microspheres.

As used herein, the terms "microparticles," "microspheres," and "particles" are interchangeable and have the same meaning except when specifically indicated. The term "basic microspheres" refers to a cross-linked protein microsphere (e.g., a cross-linked human serum albumin (HSA) microsphere) prior to the attachment of fibrinogen, or to that part of a fibrinogen-coated microsphere that existed prior to the attachment of fibrinogen.

Use as Therapeutic Agent

The invention provides fibrinogen-coated particles useful as a therapeutic agents. The compositions dramatically reduce bleeding time when administered to thrombocytopenic animals. Thus, one example of therapeutic use is to inject or infuse the composition of the invention intravenously for the purpose of decreasing bleeding time in humans or nonhuman animals.

The compositions of the invention may be administered to ameliorate a variety of conditions and diseases such as (but not limited to) thrombocytopenia (including thrombocytopenia resulting from radiation exposure or chemotherapy), platelet dysfunction due to kidney failure, drug sensitivity, drug action (e.g., aspirin) or as a result of cardiopulmonary bypass, as well as other conditions (e.g., an antiplatelet immune response) in which reducing bleeding time and blood loss will be beneficial to the patient. Treating patients who have developed resistance to platelet transfusion is of particular value. In general, any platelet related disease, whether caused by low platelet levels or platelet dysfunction despite platelet levels being normal, is treatable by the methods and compositions disclosed herein. In addition, it is anticipated that in patients about to undergo surgery with major blood loss, or in trauma patients, even though they have a "normal" platelet count, administration of the compositions of the invention will decrease blood loss and lead to shortened surgical time.

As used herein, the terms "treatment" or "treating" of a condition and/or a disease in a mammal, means (i) preventing the condition or disease, that is, avoiding any clinical symptoms of the disease, (ii) inhibiting the condition or disease, that is, arresting the development or progression of clinical symptoms; and/or (iii) relieving the condition or disease, that is, causing the regression of clinical symptoms. The terms "therapeutically effective dose" or "pharmacologically effective amount" are well recognized phrases and refer to that amount of an agent effective to produce the intended pharmacological result. Thus, a therapeutically effective amount is an amount sufficient to ameliorate the symptoms of the disease being treated, e.g., thrombocytopenia.

Administration of the compositions of the invention can be via any accepted systemic or local route (for example, via parenteral, transdermal or topical routes) but usually will be by intravenous injection or infusion. The actual dose of microspheres administered will depend on the disease condition being treated, the health of the patient, and other factors. It is expected that a dose will comprise between about $10^7$ and $10^{12}$ microspheres per kg, more often between about $10^9$ and $10^{11}$ microspheres per kg. As is disclosed in the Examples, infra, smaller doses may have increased efficacy when more than one dose is administered. Thus, in one embodiment of the invention, the microspheres are administered as at least two doses. In one embodiment, the second dose is administered within about 24 hours after administering the first dose; an a related embodiment, the second dose is administered within about 12 hours after administering the first dose. Actual methods of preparing such dosage forms are known, or will be apparent, to those skilled in this art. The composition to be administered will, in any event, contain a quantity of microspheres in a pharmaceutically effective amount for relief of the particular condition being treated in accordance with the teachings of this invention.

Prior to injection or infusion, the microspheres may be (re)suspended in an excipient (e.g., by adding a concentrated excipient solution to a microsphere solution or to a preparation before an optional lyophilization step). A variety of suitable excipients are known or can be prepared (see, for example, *Remington's Pharmaceutical Sciences*, Mack Publishing Company, Easton, Pa., 16th Ed., 1980). Typically the excipients comprise one or more of polyethylene glycol (e.g., 0.5%–3% PEG 3350 or PEG 8000), citrate (e.g., 0.5 mM–10 mM), EDTA (e.g., 1 mM), arginine (e.g., 0.1 M), mannitol (e.g., 2%), lactose (e.g., 1–4%), maltose (e.g., 1–4%), Pluronic F-68 (e.g., 5%), carboxymethylcellulose (e.g., 1.5%) and a detergent (e.g., 0.01–0.5% Tween-80®, a non-ionic detergent). A most preferred excipient is: arginine (2.1%), maltose (2.0%), lactose (2.0%), citrate (0.0105%), EDTA (0.0186%), Tween 80 (0.01%), pH 6.4 (adjusted with 0.1 N sodium hydroxide solution). Another preferred excipient is: 0.1M arginine, 5 mM citrate, 0.5 mM EDTA, 1% lactose, 1% maltose and 0.1% Tween-80®). When used with a preparation of microspheres that is lyophilized and subsequently resuspended, an excipient is chosen that provides a reconstitution time of less than about 10 minutes, more often less than 5 minutes, and results in minimal formation of aggregates.

The compositions of the invention are nontoxic when administered by injection or infusion. As used herein, "toxicity" includes acute toxicity and chronic toxicity. It will be readily apparent that the composition of the invention are preferably virus-free and nonpyrogenic. In addition, toxicity can be assessed in studies using animals (e.g., mice, rats and rabbits). The compositions of the present invention exhibit minimal toxicity in animals. Evidence of non-toxicity includes absence of adverse clinical signs such as: cardiac problems (e.g., heart failure, coronary perfusion deficiencies, neutrophil infiltration), pulmonary problems (embolism, desaturation of oxygen tension in erythrocytes, multifocal edema and intravascular hyalin spheres in the lung, proliferative multifocal pneumonitis), renal failure or congestion, congestion of or percholangial mononuclear cells in the liver, clinical laboratory values not within normal limits (e.g., hematology, coagulation profiles, liver and renal function tests), hyalin thrombus in the iris, mononuclear cells in the choroid of the eye, and multifocal degeneration of myofiber. Other signs of toxicity include weight loss, prostration, lethargy and death.

Physical Characteristics

The protein particles which are the subject of this invention are generally monodisperse particles, generally spherical in shape. In a most preferred embodiment the particle comprises a basic microsphere of cross-linked human serum albumin coated with human fibrinogen.

The term "monodisperse" as used herein denotes discrete single particles which are individually suspended in the aqueous suspension and are neither attached nor adhered to other particles, as distinct from aggregates or aggregated particles, which are groups of two or more, and as many as a hundred or more, such particles adhering to each other by surface interaction or attraction, the aggregates themselves being suspended in the medium in the same manner as the monodisperse particles. While large aggregates can be discerned by the naked eye, a microscope is generally required to differentiate mid-size to small aggregates from monodisperse particles.

The protein particles of the invention have a sponge-like internal structure with fenestrations on the surface leading to the internal matrixes. The fenestrations can be visualized by transmission electron microscopy as described in the Examples. Upon attachment of fibrinogen to the basic particles the fibrinogen coats the exterior surface of the microsphere. It is believed that the fibrinogen also enters the "interior" of the sphere, although this is difficult to demonstrate experimentally.

The size range of the particles of the present invention primarily range from about 50 to about 5000 nanometers in diameter, in monodisperse form. In a preferred embodiment, the particles are primarily (e.g., at least about 70, 80, 90, 95, or 99% by number) between about 100 nm and 5000 nm in diameter, more preferably between about 100 nm and 2000 nm in diameter. In one embodiment, as is shown in the Examples, infra, most (i e., more than 50%) of the particles are between 100 nm and 500 nm in diameter; a substantial portion (e.g., at least about 15–20%) are about 1000 nm (range about 500 nm to about 1700 nm) in diameter.

The compositions of the invention are substantially free of large particles. Thus, usually the composition will comprise, per billion ($10^9$) particles in solution less than about $0.05 \times 10^6$ particles greater than 25 $\mu$m in diameter, more often less than about $0.01 \times 10^6$, still more often less than $0.005 \times 10^6$ particles. Usually the composition will comprise, per billion ($10^9$) particles less than about $3 \times 10^6$ particles greater than 7 $\mu$m in diameter, more often less than about $1 \times 10^6$, still more often less than $0.5 \times 10^6$ particles, most often less than about $0.05 \times 10^6$; and often even less, such as $0.001 \times 10^6$ or less.

The compositions of the invention are substantially free of aggregates. Thus, usually the composition will comprise, per billion ($10^9$) particles less than about $0.1 \times 10^6$ particles greater than 25 $\mu$m in diameter, more often less than about $0.05 \times 10^6$.

Thus, in one embodiment, at least about 50% (by number) of the microspheres in the suspension are between about 100 and about 500 nanometers in diameter, and at least about 10% are between about and 500 nm and about 1700 nm in diameter. In another embodiment, at least about 90% of said microspheres are between about 100 and about 500 nanometers in diameter. In another embodiment, at least about 90% of said microspheres are between about and 500 nm and about 1700 nm in diameter. In some embodiments, suspension has fewer than about $3 \times 10^6$ microspheres (or microsphere aggregates) greater than 7 $\mu$m in diameter per $10^9$ microspheres. In still other embodiments, the suspension has fewer than about $10^5$ microspheres (or microsphere aggregates) greater than about 25 $\mu$m in diameter.

In measuring the number of large particles or the number of aggregates in a composition of the invention particles are measured using a Coulter Multisizer II (with a 30 micron diameter orifice) or the equivalent. (As noted infra this apparatus undercounts particles with a diameter of less than about 0.6 $\mu$m.) Alternatively, the measurement of microparticle sizes (of all size ranges) can be carried out by examining a sample by microscopy (e.g., transmission or scanning electron microscopy) and comparing the microspheres to a standard(s) of known size(s). The size, or size distribution, of small particles can be determined in a variety of ways, for example using a HIAC liquid particle counter (Pacific Scientific Company /HIAC/ROYCO Division, Silver Spring, Md). One suitable counter is a 8000A counter (cat. no. 033X207-01) fittered with a microcounter-100 sensor (cat. no. MC100) and a 3000A sampler (cat. no. 084X200-01).

The measurement of large particles can be made in a liquid such as water, saline, or an excipient (e.g., after manufacturer and removal of the desolvating and cross-linking agents). Alternatively, the particles can be lyophilized and reconstituted in an excipient. Although, as described herein, a variety of excipients are useful for administration of the compositions of the invention, for the purposes of measuring aggregates and large particles, the preferred excipient is: 0.1M arginine, 5 mM citrate, 0.5 mM EDTA, 1% lactose, 1% maltose and 0.1% Tween-80.

As is discussed in detail infra, the binding of fibrinogen to the basic microsphere is stabilized by the addition of a cross-linking agent such as glutaraldehyde. However, fibrinogen may additionally be bound noncovalently to the microspheres, e.g., by hydrophobic bonding. Without intending to be bound by any particular mechanism, fibrinogen may become associated with the hydrophobic sites of the core component molecules (e.g., albumin). Microspheres of the invention often comprise more than a monolayer of fibrinogen molecules on the surface of the sphere. Typically, one or more layers of fibrinogen molecules covalently bound to the sphere surface may be accompanied by additional layer(s) that adhere via a hydrophobic or electrostatic interaction.

The amount of fibrinogen associated with the microsphere of the invention (i.e., fibrinogen per microsphere) will vary according to the size distribution of the microspheres (because larger diameter microspheres have larger surface areas). In a preferred embodiment the microspheres of the invention will have at least about (on average) $4 \times 10^{12}$ molecules of fibrinogen per $10^9$ spheres, more often at least about $5 \times 10^{12}$ molecules of fibrinogen per $10^9$ spheres, even more often at least about $10 \times 10^{12}$ molecules of fibrinogen per $10^9$ spheres, and most often at least about $15 \times 10^{12}$ molecules of fibrinogen per $10^9$ spheres. As will be apparent to those of skill, quantitation of fibrinogen can be carried out, as described in the Examples, by measuring fibrinopeptide A (see, e.g., Soria et al., 1980, *Thrombosis Research*, 20:425 which is incorporated herein by reference in its entirety and for all purposes as well as by other methods).

Method of Making

The particles of the invention may be produced according to methods described in U.S. Pat. No. 5,069,936, with modifications and additions described infra. Useful particles are also described in International (PCT) Application WO 96/39128, and commonly assigned patent applications U.S. Ser. No. 08/471,650 and U.S. Ser. No. 08/554,919. Each of the aforementioned patents and applications is incorporated herein by reference in its entirety for all purposes.

In a first embodiment, the particles of the invention are made by (i) adding a desolvating agent to an aqueous mixture of a protein and a surfactant, whereupon a turbid mixture comprising substantially monodisperse protein microspheres results; (ii) adding a first crosslinking agent to the turbid mixture; (iii) removing large particles and aggregates from the mixture; (iv) adding a second cross-linking agent, which may be the same as the first cross-linking agent; and (v) immediately adding fibrinogen.

In a preferred embodiment, the protein is serum albumin, with human serum albumin most preferred, the surfactant is Sotradecol (sodium tetradecyl sulfate), the desolvating agent is an alcohol, with ethanol most preferred, both the first and second cross-linking agents are polyaldehydes, with glutaraldehyde most preferred, the fibrinogen is human fibrinogen, and the step of removing large particles and aggregates from the mixture comprises filtering or centrifuging the mixture.

In a second embodiment, the particles of the invention are made by (i) adding a desolvating agent to an aqueous mixture of a protein and a surfactant, whereupon a turbid mixture comprising substantially monodisperse protein microspheres; (ii) adding a crosslinking agent to the turbid mixture; (iii) adding fibrinogen to the mixture whereupon the particles are coated with the fibrinogen; and (iv) removing large particles and aggregates from the mixture.

In a preferred embodiment, the protein is serum albumin, with human serum albumin most preferred, the surfactant is sodium tetradecyl sulfate, the desolvating agent is an alcohol, with ethanol most preferred, the cross-linking agent is a polyaldehyde, with glutaraldehyde most preferred, the fibrinogen is human fibrinogen, and the step of removing large particles and aggregates from the mixture is carried out by centrifugation.

It should be noted that the first and second embodiments, supra, provide essentially the same composition, i.e., a suspension of cross-linked protein (HSA) microspheres with attached fibrinogen, substantially free of large particles and aggregates.

Protein Components

The protein forming the basic microsphere should be non-toxic in humans, and preferably is substantially nonimmunogenic. In a preferred embodiment the protein is human serum albumin (HSA). In alternative embodiments, other polypeptides, such as truncated HSA polypeptides, may be used. The HSA may be of human origin (e.g., purified from human serum) or may be recombinantly produced (e.g., from prokaryotic or eukaryotic cells transfected with a gene encoding HSA).

The fibrinogen coating the basic microsphere is preferably human fibrinogen which may be purified from human blood products or produced by other means (e.g., recombinantly). In some embodiments, fibrinogen variants (e.g., genetically engineered or proteolytic products) are used (see, e.g., Rooney et al., *J Biol Chem* 271:8553, 1996). In other embodiments, peptides or polypeptides which contain reactive sequences of fibrinogen, such as asparagine-glycine-aspartic acid (RGD) are used.

Removal of Large Particles

In one embodiment, the basic microspheres (i.e., prior to addition of human fibrinogen) are subjected to a filtration step to remove spheres larger than about 7 μm diameter and aggregates of spheres. A filter that retains particles greater than about 5 microns is preferred (e.g., a Membrex Pacesetter Pilot Filter System 400 $cm^2$ [cat. # pspilot] fitted with a 3 μm [cat. # 3039-003] or 5 μm [cat. # 3039-005] SteelPore 400 $cm^2$ Cartridge, Membrex Inc., 155 Route 46 West, Fairfield, N.J. 07004) or a similar filtering system.

The filtrate can then be concentrated and dialyzed (e.g., using a 0.2 micron Asahi hollow fiber cartridge [Plasmaflo AP-05HL, Asahi Medical Co.] or similar device). The device should permit separation of large molecules (such as HSA or large polymers from the microsphere solution. It is believed that removal of residual HSA permits more efficient binding of the fibrinogen to the basic microsphere.

It is desirable that the filtration and dialysis systems be designed to avoid clogging by the concentrated microsphere suspension.

Large particles and microspheres can also be removed by centrifugation, which may be carried out either before or after the attachment of fibrinogen to the basic microsphere. For example, centrifugation at a relative centrifuge force of 4000×g, for 30–180 seconds (Model Marathon 21K from Fisher Scientific, with a 16 cm rotor holding 50 mL conical tubes) is effective at removing large (e.g., >10 micron) particles. In some cases it will be desirable to use a continuous centrifugation system (e.g., Alpha Laval BTX205 continuous centrifuge) to improve production efficiency.

Mechanism of Action

The mechanism(s) by which the compositions of the invention exert clinical effects have not been fully elucidated and it is possible that multiple mechanisms are involved. Without intending to be bound by particular theory or mechanism, the antithrombocytopenic effects of the microspheres of the invention may related to one or more of the following mechanisms: (1) thrombin at a wound site cleaves the fibrinogen on the surface of the microspheres, promoting formation of fibrin crosslinks with fibrin on the surface of activated platelets; (2) soluble plasma fibrinogen is activated by thrombin and cross-links microspheres to other microspheres and microspheres to platelets; with the spheres adding passively to the bulk of the clot; (3) microspheres (having a high local concentration of fibrinogen per surface area) are able to send signals across the platelet membrane (e.g., via a fibrin(ogen) receptor). See commonly assigned patent application U.S. Ser. No. 60/048,747 entitled "Modification of Platelet Action by Fibrinogen-Coated Microspheres" (attorney docket number 016197-001600) filed Jun. 5, 1997 which is incorporated by reference herein in its entirety and for all purposes; (4) an interaction between the infused microspheres and the endothelium may occur. In regard to these mechanisms (especially 3 and 4) it is notable that while pharmacokinetics studies have shown that after infusion of radiolabeled microspheres (preparations comprising large particles, see Examples infra), most radioactivity disappears from the intravascular compartment within minutes, the effect of the infusion (e.g., reduced bleeding time) persists for 3 to 4 days.

EXAMPLES

I. Introduction

II. Materials and Methods
A. Reagents
B. Animal studies
C. Preparation of Fibrinogen-Coated Microspheres
D. Large Scale Synthesis of TS1, TS2, TS3 and CS
E. Filtration Apparatus for TS2 and TS3
D. Characterization of Microspheres (Assays 1–16)

III. Results

Efficacy
A. Reduction in Bleeding Time in Thrombocytopenic Rabbits
B. Hemostatic Function of TS1 and TS3
C. Reduction in Blood Loss in Thrombocytopenic Rabbits
D. Effect of Repeat Dose Safety
A. Thrombogenic Potential
B. Serotonin Release Pharmacokinetics Particle Size and Filtration
A. Effect of Filtration on Size Distribution
B. Fibrinogen Loss During Filtration Removal of Large Particles by Centrifugation Aggregation of Platelets and Microspheres TS Structure "Release" Assays Stability of TS During Storage at 4° C.

INTRODUCTION TO EXAMPLES

These examples describe the preparation and characterization of fibrinogen-coated albumin spheres made by three different methods, with the resulting products referred to as TS1, TS2 and TS3. Surprisingly, preparation TS3 had superior characteristics and is both an efficacious and nontoxic synthetic platelet. It is believed that the anti-thrombocytopenic properties of TS3 are generally the same as those measured for TS1 but with improved properties.

Materials and Methods
Reagents
Human serum albumin (HSA) USP (25%) and human fibrinogen (as a lyophilized powder, viral-inactivated but not heat-treated) were purchased from Alpha Therapeutics, Calif. Sotradecol (a brand of sodium tetradecyl sulfate, USP) was purchased from Elkins-Sinn, Inc. Ucarcide (a brand of glutaraldehyde, 25% USP) was purchased from Union Carbide, Conn. Citric Acid (USP), EDTA (Ultrapure), lactose (NF), Tween80® were bought from J T Baker, N.J. Arginine was from Sigma Chemical Company (Mo) and maltose was from Mallinckrodt, Conn.

Animal Studies
Bleeding time and blood loss measurements were done according to published protocols (see, e.g., Blajchman and Lee, 1997, *Transfusion Med. Reviews* 11:95–105). Thrombogenicity tests were carried out according to Wessler et al., 1959, *J. Appl Physiol.* 14:943–6.

Preparation of Fibrinogen-Coated Microspheres
Fibrinogen-coated albumin microspheres were prepared by three different methods as described infra. The particles are referred to as "TS1," "TS2," and "TS3." "CS," or "control spheres" are protein microspheres not coated with fibrinogen. Table 1 correlates the particle names with specific production lot numbers and a brief description.

TABLE 1

| Particle Designation | Lot Number | Fibrinogen Attached |
| --- | --- | --- |
| CS | — | No |
| TS1 | Lot K9401 | Yes |
| TS2 | Lot 22.026 | Yes, before filtration |
| " | Lot 22.029 | |
| TS3 | Lot 22.033 | Yes, after filtration |
| " | Lot 22.038 | " |

The TS preparations used in these examples were prepared by the methods described infra. The methods are first described in general terms followed by a description of production using a production apparatus.

1) HSA, 25% USP was first diluted with normal saline (0.9% sodium chloride solution USP), and Sotradecol (3% USP) was added to a final concentration containing 15% HSA (w/v) and 0.002% (v/v) of Sotradecol (this mixture hereafter referred to as sHSA) (Note that the volumes of each ingredient subsequently added were multiples or fractions of the initial volume of Sotradecol containing-15% HSA used, which was defined as "one volume");

2) 1.0 volume of the above mixture (sHSA) was mixed quickly with 1.8 volume of 70% ethanol (with the remainder volume 30% injection-grade water), at which time turbidity was immediately observed;

3) 0.11 volume of 1.25% glutaraldehyde (diluted from a 25% Ucarcide225 stock with normal saline) was mixed into the turbid suspension immediately;

4) Thereafter, for TS1 and TS2, a 1.45 volume of fibrinogen solution (1.0 mg/ml, diluted from a stock of 10 mg/ml dissolved with water) was mixed in within 10 minutes to coat the spheres in the presence of glutaraldehyde.

For TS3, normal saline was substituted for the fibrinogen solution in this step.

Steps 1–4 were carried out at room temperature.

5) The bulk suspension was then placed in a cold room (about 4° C.) and stirred slowly (40±10 rpm) in the final bulk container by placing the unopened container on a moving platform until the step for filling into glass bottles or filtration was ready to proceed.

6) For TS2, the fibrinogen-containing sphere suspension was subjected to the filtration step using a 5 micron Membrex Filter System to remove large particles. The retentate was discarded. The filtrate was then concentrated with a sterile 0.2 micron Asahi hollow fiber cartridge (Plasmaflo, AP-05HL). Aseptic techniques were consistently used.

For TS3, the sphere suspension (containing no fibrinogen) was filtered with either a 3 micron (Lot 22.033) or a 5 micron (Lot 22.038) Membrex Filter System. The filtrate was then concentrated with a sterile 0.2 micron Asahi hollow fiber cartridge. Aseptic techniques were used.

7) For TS3, glutaraldehyde (1.25%) was added to a final concentration of 0.05%, immediately followed by addition of a fibrinogen solution (1 mg/ml) with mixing to result in a final concentration of 0.33 mg/ml fibrinogen.

8) Before filling glass prescription bottles with any of the three TS preparations, samples of the respective suspensions were taken aseptically to measure with the Coulter Multisizer the concentration of TS. Additional sterile normal saline was added to adjust the concentration of spheres to about $3\times10^9$ TS/ml or less. Thereafter TS1 was lyophilized. The presence of residual soluble HSA in the supernatant obviated the need for addition of excipient for TS1. For TS2 and TS3, a 5-fold concentrated solution of excipients was added (1 part per 4 part of adjusted suspension volume) to result in the following final concentration of excipients: arginine (2.1%), maltose (2.0%), lactose (2.0%), citrate (0.0105%), EDTA (0.0186%), Tween 80 (0.01%). Sodium hydroxide solution (0.1N) was used to adjust the pH to 6.4.

9) Aseptic filling was performed in a class 100 laminar flow hood. After filling the bottles with the designated volume of the formulated suspension, the contents were lyophilized to dry powders containing less than 4% of moisture. The lyophilized TS were stored in the refrigerator (about 4° C.) until use.

10) To resuspend, normal saline (for TS1, TS2 and CS) or water (for TS3) was injected into the vials with a syringe and needle for reconstitution into suspensions. After no solid particles remain visible to the eye, samples of the suspension were subjected to some of the release assays described infia, or for animal studies.

CS were produced as for TS1, except that normal saline was added in place of the fibrinogen solution at step (4).

Large Scale Synthesis of TS1, TS2, TS3 and CS

A method for efficiently achieving instantaneous and thorough mixing of solutions to produce non-aggregated protein spheres has been disclosed in PCT publication WO 96/40075. This method also allows specific ingredients to be added aseptically and at a specified time in a sequenced manner. FIG. 1 illustrates the general layout of the apparatus used.

For the manufacture of TS1 (Lot K9401) and TS2 (Lots 22.026 and 22.029), four ingredient bags (each having one 0.2 micron Gelman hydrophilic filter capsule attached to ensure sterility of the infilling solution) and one 20- (or two 10-) liter receptacle bags (to hold a total of 10 to 20 L of concentrated TS suspension before the addition of excipients) were needed. After the bags were connected to the proper length of silicon tubing (0.25 inch inner diameter), the entire manifold assembly was gamma irradiated to ensure sterility of the bags and the connections. The following volumes of ingredient solutions (or a comparable ratio in volume) were pumped into the bags:

1. First (5L) bag was filled aseptically with 3433±172 ml of sHSA (premix 2060 ml of HSA, 25%, USP with 1371 ml of normal saline, plus 2.3 ml of Sotradecyl, 3%)
2. Second (10L) bag was filled aseptically with 6180±309 ml of 70% ethanol (premix 1854 ml of sterile water for irrigation, USP with 4326 ml of dehydrated ethanol, 100% USP)
3. Third (1L) bag was filled aseptically with 769±39 ml of diluted 1.25% glutaraldehyde (premix 38.4 ml of Ucarcide225, USP with 730.8 ml of normal saline, USP)
4. Fourth (10L) bag was filled with 5285±264 ml of a 1 mg fibrinogen/ml solution (premix 530 ml of a 10 mg fibrinogen/ml in water with 5280 ml of normal saline, USP).

Four peristaltic pumps (Watson Marlow, Model 505Du or 505Di/L) were used to accurately deliver the ingredient solutions to the respective Mixing Junctions. Pump One was turned on to pump sHSA from First Bag at a rate of 125 ml/min to the first Mixing Junction at which time Pump Two was turned on to pump the 70% ethanol solution from Second Bag at a rate of 225 ml/min to cause rapid mixing of the two solutions. Turbidity was seen immediately inside the tubing. The turbid front of the suspension was designed to reach Second Mixing Junction within 5 minutes, at which time Pump Three was turned on to pump the 1.25% glutaraldehyde from the Third Bag at a rate of 14 ml/min to stabilize the spheres. As the turbid front of the stabilized spheres reached the Third Mixing Junction, typically within another 10 minutes, Pump Four was turned on to pump the fibrinogen solution at a rate of 182 ml/min into the suspension.

At the time First bag was about to become empty, Pump Two was first turned off to stop the synthesis of spheres, then Pump Three, then Pump Four, all with a time interval similar to that with which they were first turned on, so that the material inside the tubing (ongoing process) was not wasted. When the tail end of the turbid suspension was pumped into the receptacle bags, Pump One was turned off.

After the fibrinogen-coated TS was stabilized, aliquots of the TS1 suspension were filled into glass prescription bottles within 24 hours, as described infra; whereas the TS2 suspensions were subjected to a filtration step (described infta).

The concentration of spheres (e.g. $Y\times10^9$/ml) in the non-formulated suspension was then measured (typically 5 to $10\times10^9$ spheres/mL.) The volume of suspension to fill each bottle was calculated using the formula: 10 ml×2.5/Y. Ethanol was removed during the lyophilization process. After reconstitution with 10 ml of normal saline, the concentration of spheres was verified to be $2.5\times10^9$ TS/ml for K9401 and $2.8\times10^9$ TS/mL for both Lot 22.026 and Lot 22.029.

CS were synthesized using the method for TS1 except that normal saline was used instead of fibrinogen solution in step 4. Sphere suspensions obtained at this stage had essentially the same physical characteristics as TS1 (Lot K9401) except without fibrinogen.

TS3 were synthesized using the method for TS1 except that normal saline was used instead of fibrinogen solution in step 4 with the following additional steps: the sphere suspension (non-fibrinogen-containing spheres) was filtered with either a 3 micron Membrex system (Lot 22.033) or a 5 micron Membrex system (Lot 22.038) and concentrated with Asahi hollow fiber cartridges to achieve a final volume of approximately 2.8 volume (see infra). Subsequently, a volume of 1.25% glutaraldehyde was added to achieve a final concentration 0.05%, followed immediately with the addition of a 1.45 volume of fibrinogen solution (1 mg/ml) to achieve a final concentration of 0.33 mg/ml. Thereafter the concentration of spheres was measured and additional normal saline (if needed) and excipients were added so that the final concentration of spheres after lyophilization in the presence of excipients and after reconstitution with 4 ml of water per vial was 1.6 and $3.0\times10^9$ particles per ml, respectively, for Lot 22.033 and Lot 22.038.

Filtration Apparatus for TS2 and TS3

Figure 2:
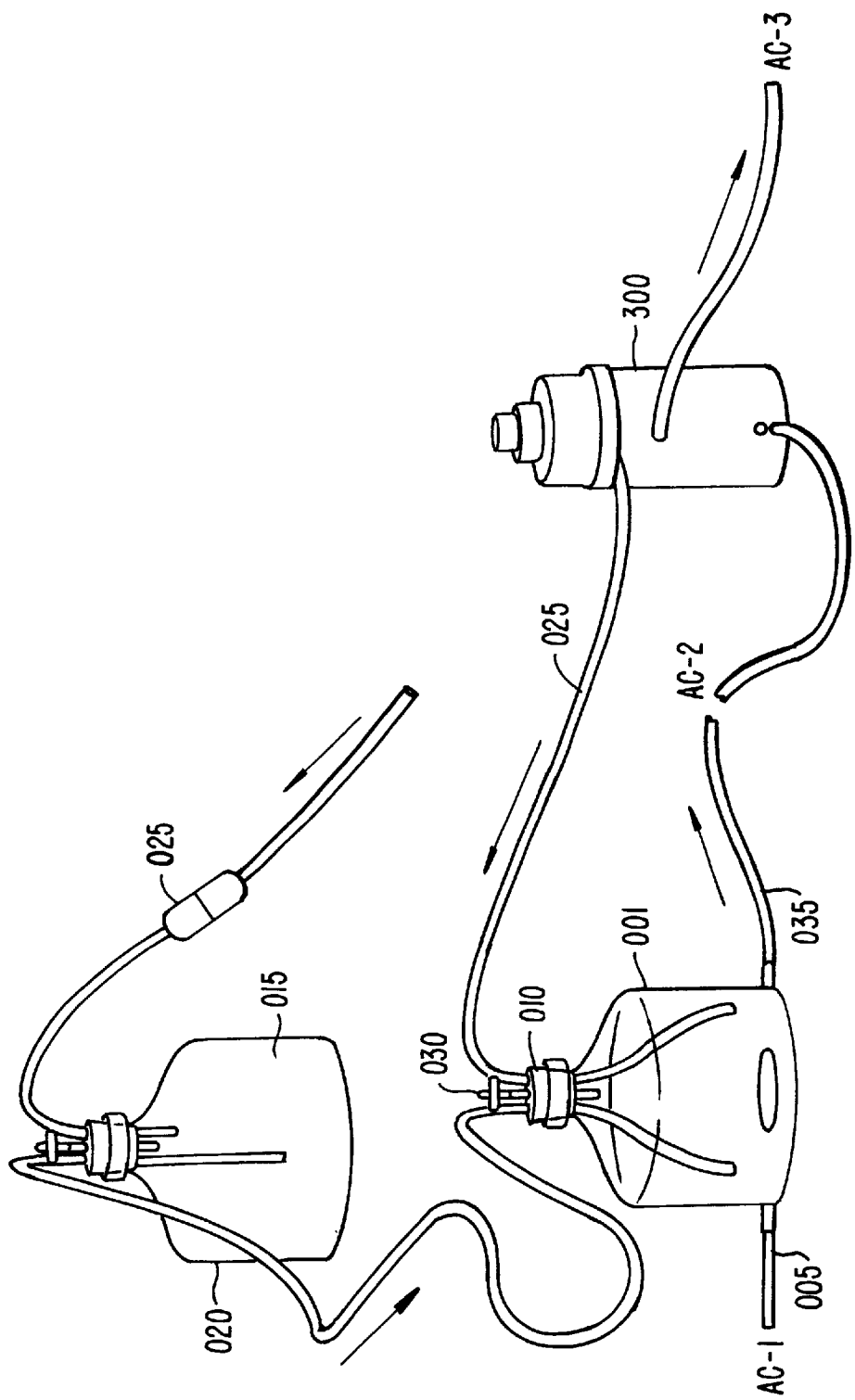
FIG. 2 shows an apparatus for filtration of the microspheres.

To remove particles larger than 3 or 5 micron in diameter (for TS2 and TS3), the following additional steps were taken:

FIG. 2 illustrates a 10 L glass bottle (001) with inlet (005) which was connected via an aseptic connection (AC-1) to the outlet of the receptacle bag containing the non-formulated TS. The bottle was covered with a sterile stopper (010) through which a sterile dialysate solution (015) in another 10 L glass bottle (020) could be drawn to keep a certain volume within glass bottle (001). The same stopper (010) had two additional inlets: one for the inflow of retentate (025) and another for the venting of air via a sterile filter (030). The glass bottle (001) had an outlet (035) which was aseptically connected to the Membrex System (300) via the aseptic connection (AC-2). The Membrex System had an outlet which allowed the filtrate (containing particles expected to be smaller than 3 or 5 microns) to be connected via a third aseptic connection (AC-3) to the Asahi hollow fiber cartridge (in FIG. 3). A peristaltic pump (not shown in FIG. 2) was placed between AC-2 and the glass bottle (001) to pump the TS suspension into the Membrex System (the Mini-Pacesetter model was used which was rotated at a rate of 900±100 rpm.) The filter used was 3 micron for Lot 22.033 and 5 micron for Lot 22.026, Lot 22.029 and Lot 22.038. An optional C-clamp was placed across the retentate tube to regulate (if necessary) the back pressure on the retentate to keep the flux rate (flow rate of filtrate out of the Membrex system) to be about 50% that of the retentate flow rate. It was easiest to monitor flux and retentate flow by observing the two input streams to the glass bottle (001): the retentate flow rate is the rate of fluid return from the Mini-Pacesetter; the flux rate being equal to the dialysate flow into the bottle (001) from reservoir container (020). Typically the concentration of TS in bottle (001) was first diluted with the dialysate to reduce the chance of clogging the Membrex system. As more filtrate left the system, an equal volume of dialysate would be drawn into the bottle (001). The inlet to reservoir (020) had a filter (025) to ensure the sterility of air entering the reservoir. When the dialysate (a 0.45% sodium chloride solution was used) was depleted, the filtration operation was continued until the fluid level inside bottle (001) reached the top of the stir bar, or until the flux was reduced to zero because of filter plugging.

Figure 3:
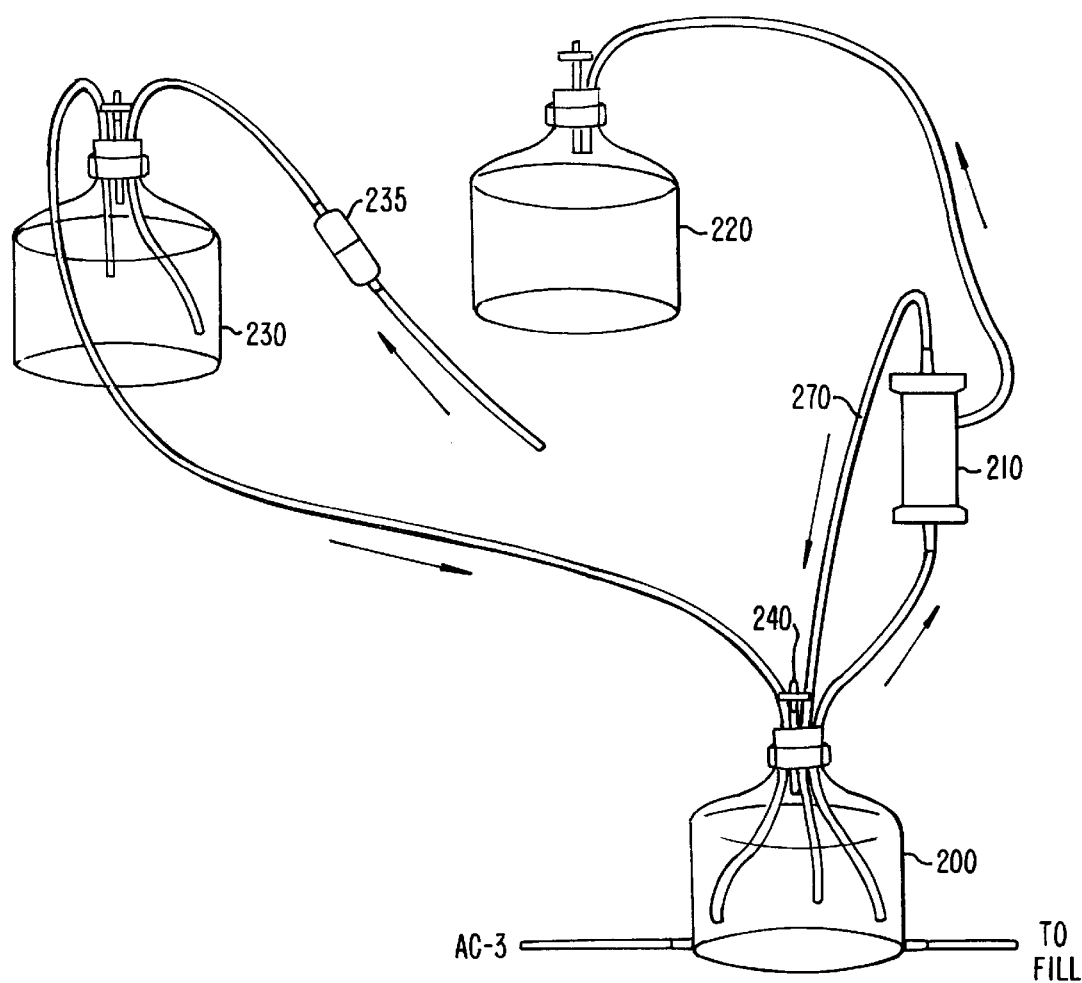
FIG. 3 shows an apparatus for concentrating and the diafiltering microspheres.

FIG. 3 illustrates the apparatus used for concentrating and the diafiltering (i.e., also referred to as "dialysis") the final product. A 10L glass bottle (200) had an inlet tubing with an aseptic connection AC-3 which could be connected to the incoming "post-Membrex" suspension which was pumped into the bottle (200) by a peristaltic pump (not shown in FIG. 3). The suspension in bottle (200) was then pumped by another peristaltic pump (not shown in FIG. 3) placed between this bottle (200) and the Asahi hollow fiber cartridge (210, Plasmaflo AP-05HL, manufactured for plasmapheresis, with molecular exclusion large enough for proteins such as albumin and antibodies to filter through). The filtrate was pumped into the "waste liquid" bottle (220). The retentate (270) was recycled into bottle (200). As the volume inside glass bottle (200) decreased to a level desired to achieve the desirable concentration of spheres, the vent (240) on top of the bottle was clamped off to create a partial vacuum which would draw water from the reservoir (bottle 230) to keep a constant volume of suspension inside bottle (200.) The reservoir (230) held a volume of water at least twice the volume of the suspension in bottle (200) and had a filter (235) which sterile-filtered the incoming air into bottle (230.) Thus the desirable reduction in the volume of suspension and the replacement of soluble material in the supernatant (replaced mostly by water) by diafilitration could be achieved. Thereafter, the concentration of the spheres were measured and the excipients were added. The formulated suspensions were then filled into prescription bottles and lyophilized.

Characterization of Microspheres

The following assays were used to determine the properties of microspheres made by various methods.

1. Fibrinopeptide A (FPA) Concentration:

Lyophilized TS1, TS2, and TS3 were reconstituted as specified and a fraction was centinfuged at 12,000×g for 10 mim to obtain the orresponding su pernatant fraction for comparison. Thrombin solution (100 NIH units/ml) was added to release FPA from the either the whole suspension or the supernatant fraction, according to a competitive enzyme-linked immunoassay method (Soria et al., 1980, *Thrombosis Research*, 20:425). The difference between the FPA released from the whole suspension and that from the supernatant was the FPA on the spheres, expressed as ng/ml of suspension, or $ng/10^9$ spheres.

2. Size and Concentration of TS:

Unless otherwise specified, a Coulter Multisizer II (Coult er Corp. Scientific Inst., P.O. Box 2145, Hialeah Fla. 33012-0145) fitted with a 30 micron diameter orifice (Coulter Cat. No. CEI 6102030 [CMS 359-984]) was used to measure the average number and size of particles from three readings. However, the Coulter Multizer oI did not efficiently count or size particles smaller than about 0.6 micron in diameter, for which a HIAC (Pacific Scientific Company HIAC/ROYCO Division, Silver Spring, Md.) particle counter was employed.

To quantitate the concentration of large particles, a 20 microliter sample was introduced under the cover slip of a hemocytometer after proper dilution of the sample to yield non-overlapping particles under the visual field. This step was repeated 10 times to obtain the average of large particles in the original sample. A Hamamatsu microscope video camera C2400 was also used in conjunction with a Hamamatsu Argus-10 image processor and a Sony Trinitron C olor video monitor PVM-1343MD to record random images of the samples, after which the distributions of different particle size were measured.

3. Protein Assay:

The protein concentration in the whole suspension and that of the supernatant was measured with the Pierce Bicinchoninic Acid (BCA) method.

4. Unreacted Glutaraldehyde Concentration:

This assay was based on the formation of an imine (Schiff base) from an aldehyde in the presence of an acidic color indicating reagent.

5. Ethanol Concentration After Reconstitution:

The Sigma Diagnostics, Alcohol (ethanol), Procedure No. 332-UV was used.

6. pH of the Suspension:

A Corning 3-in-1 electrode and a Corning pH meter Model 320 were used.

7. Reconstitution Time:

After the designated volume of a diluent was injected into the vial with a syringe and needle, the vials were immediately placed on the rocking Fisher Hematology mixer. The time taken to dissociate all solid material until no obvious particulates could be seen by the unaided eye is the reconstitution time.

8. Color/Appearance:

The lyophilized products were white to light yellow in color and had the appearance of a uniform cake. The reconstituted TS appeared to be a light-yellow to yellow opaque liquid suspension with no visible foreign matter.

9. Osmolarity:

Osmolarity was tested with an Advanced Wide-Range Osmometer at room temperature.

10. Detection of Reactive Carbonyls:

CS or TS3 were first digested with pronase, pH8, overnight and then treated with dinitrophenylhydrazine (DNP). The sample was then applied to POROS R/H (hydrophobic) column to separate the products. DNP derivatives were detected at 400 nm.

11. Scanning and Transmission Electron Microscopy:

For scanning electron microscopy, samples were reconstituted with normal saline, washed in 1% cacodylate buffer, and dehydrated through graded series of alcohol to 100%. After air drying, they were sputter coated with a 60% Au/40%Pd metal for 40 seconds and examined with a Philips 505 SEM.

For transmission electron microscopy the samples were embedded in LR white and thin sectioned, followed by staining for 10 minutes in a 5% aqueous solution of uranyl acetate, and then with a 1 minute stain of lead citrate.

For immunolabeling and transmission electron microscopy, the samples were treated with either phosphate buffered saline (PBS) or a polyclonal antibody (sheep anti-human fibrinogen, purchased from Sigma Chemical Company, 1:500 dilution). After washing in PBS×3, Protein A-gold (Pelco, 10 and 20 nm size) was added. The spheres were then washed in cacodylate buffer×3, dehydrated in 60 to 100% ethanol, propylene oxide×2, 1:1 propylene oxide Eponate/Araldite, and finally in 100% Eponate/Araldite. Thin sections (50 nm) were cut with a diamond knife on an LKB Ultrotome III, placed on uncoated 400 mesh copper grids, and photographed in a Philips CM10 transmission electron microscope.

12. Bleeding Time and Blood Loss Studies:

Bleeding time and blood loss measurements were done according to Blajchman and Lee, 1997, *Transfusion Med Reviews*, 1997, 11:95–105. Briefly, severe thrombocytopenia (platelet count <$10^4$/ul) was induced in New Zealand White rabbits by sublethal gamma irradiation followed by injection of heterologous platelet antisera. Without treatment, bleeding time (BT) in these rabbits always exceeds 900 seconds (and often exceeds 60 min) for at least 72 hours post-antisera injection. For statistical purposes, it was assumed that bleeding time in untreated animals was 900 seconds (a low estimate). Blood loss was measured by infusing animals with radiolabeled erythrocytes and determining the amount of radioactivity in collected blood.

13. Thrombogenicity Potential of TS:

Thrombogenicity tests were performed according to Wessler et al., 1959, *J Appl. Physiol.* 14:943.

14. Microvascular Plugging Evaluation:

Rabbit mesentery plugging studies were performed as follows: The femoral artery of an anesthetized adult New Zealand White rabbit was exposed and ligated, after which a catheter was advanced into the femoral artery proximal to the mesentery artery and fixed into position. A midline incision was then made in the abdomen and a loop of intestine was selected and placed in a warm bath of Ringers lactate solution on the microscope stage. The 10× water immersion lens was focused on a segment of the mesenteric microcirculation. The TS suspension (or normal saline, or human platelet suspension) was infused at 5 mL/min. The flow of microcirculation was video recorded for one hour after the completion of infusion or for as long as the preparation was viable.

15. Acute Toxicity Studies:

Acute single dose intravenous toxicity studies were conducted using reconstituted lyophilized samples of TS1 (Lot K9401) and TS3 (Lot 22.038) as follows: Four groups of New Zealand White Rabbits (2/gender/group) were infused with a low, medium, high dose of the test article, and a control normal saline solution, respectively, on day 1 via a marginal ear vein. Observations were made during, and 1- and 4-hours post-infusion. Blood was collected prior to initiation at 1, 4, 24 hours post-dose and on Days 8 and 15. General observations were made daily for 14 days for clinical signs. The rabbits were sacrificed by lethal injection and a gross necropsy was performed at termination of the in-life study.

16. Pharmacokinetics:

$^{125}$I-labeling of TS was performed using the standard Iodogen method. Samples of TS were incubated with $^{125}$I-sodium iodide in Iodogenated 20 mL glass scintillation vials for 20 minutes at 22° C. with gentle agitation. Radiochemical purity was assessed using descending paper chromatography.

For TS recovery, distribution, and elimination studies, a standard dose of $7.5 \times 10^9$ $^{125}$I-TS/kg was infused into normal and thrombocytopenic male New Zealand White rabbits. The method of induction of thrombocytopenia and validation of hemostatic function of labeled TS were the same as described in Lee et al., 1995 *Blood* 86(S)). Samples of urine and feces were collected for scintillation counting using cages designed for the collection of urine. For organ distribution studies, rabbits were euthanized, and the organs were removed, weighed, and homogenized prior to scintillation counting.

RESULTS

Efficacy

A. Reduction in Bleeding Time in Thrombocytopenic Rabbits

To test the in vivo efficacy of fibrinogen-coated microspheres, the effect on bleeding time was tested using a rabbit experimental thrombocytopenia model as described by Blajchman et al., 1997, *Transfusion Med. Reviews* 11:95–105.

Figure 4:
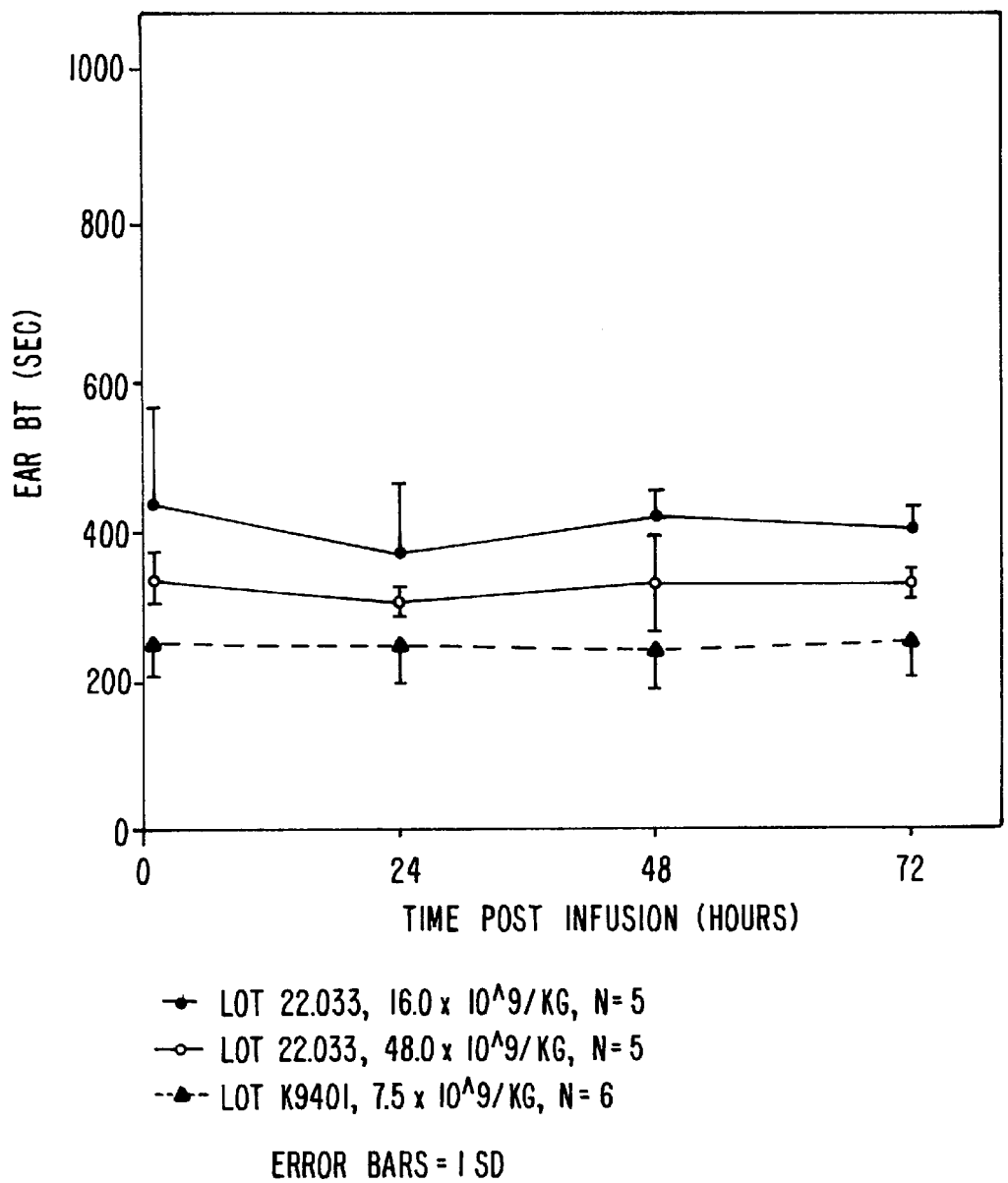
FIG. 4 shows reduction in bleeding time of thrombocytopenic rabbits.

FIG. 4 shows the reduction in bleeding time of thrombocytopenic rabbits after treatment with a single i.v. infusion of various amounts of TS3 (Lot 22.033) compared to a single dose of TS1 (Lot K9401) at $7.5 \times 10^9$ TS/kg. All the rabbits had bleeding time greater than 900 seconds prior to treatment (data not shown in FIG. 4.) TS1 (Lot K9401) appears to be at least 6.4 times more effective than these lots of TS3. CS and a normal saline control consistently showed bleeding times exceeding 900 seconds during this period (data were not shown.)

Figure 5:
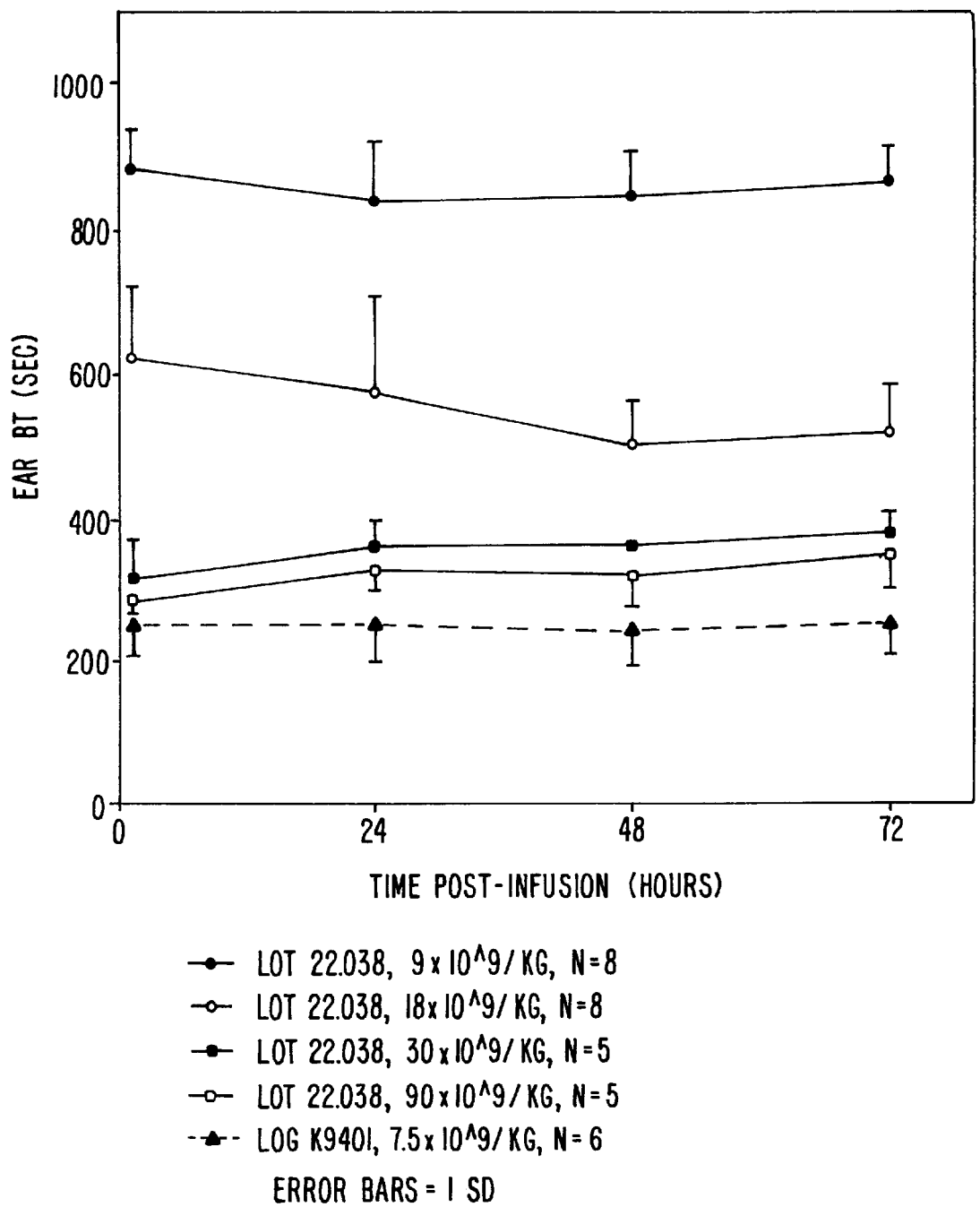
FIG. 5 shows the effect on bleeding time of TS3 (lot 22.038) compared to TS1 (lot K9401).

FIG. 5 illustrates the potency of TS3 (Lot 22.038) versus TS1 (Lot K9401) in a similar model, which showed that the potency of the former was about 4 times lower. The bleeding time between a dose of $30 \times 10^9$/kg was not statistically different from a dose of $90 \times 10^9$/kg of Lot 22.038. Thrombocytopenic rabbits infused with the supernatant obtained from Lot 22.038 (equivalent to the $90 \times 10^9$/kg dose) had bleeding times exceeding 1800 seconds during the same period (data not included in FIG. 5.)

Figure 6:
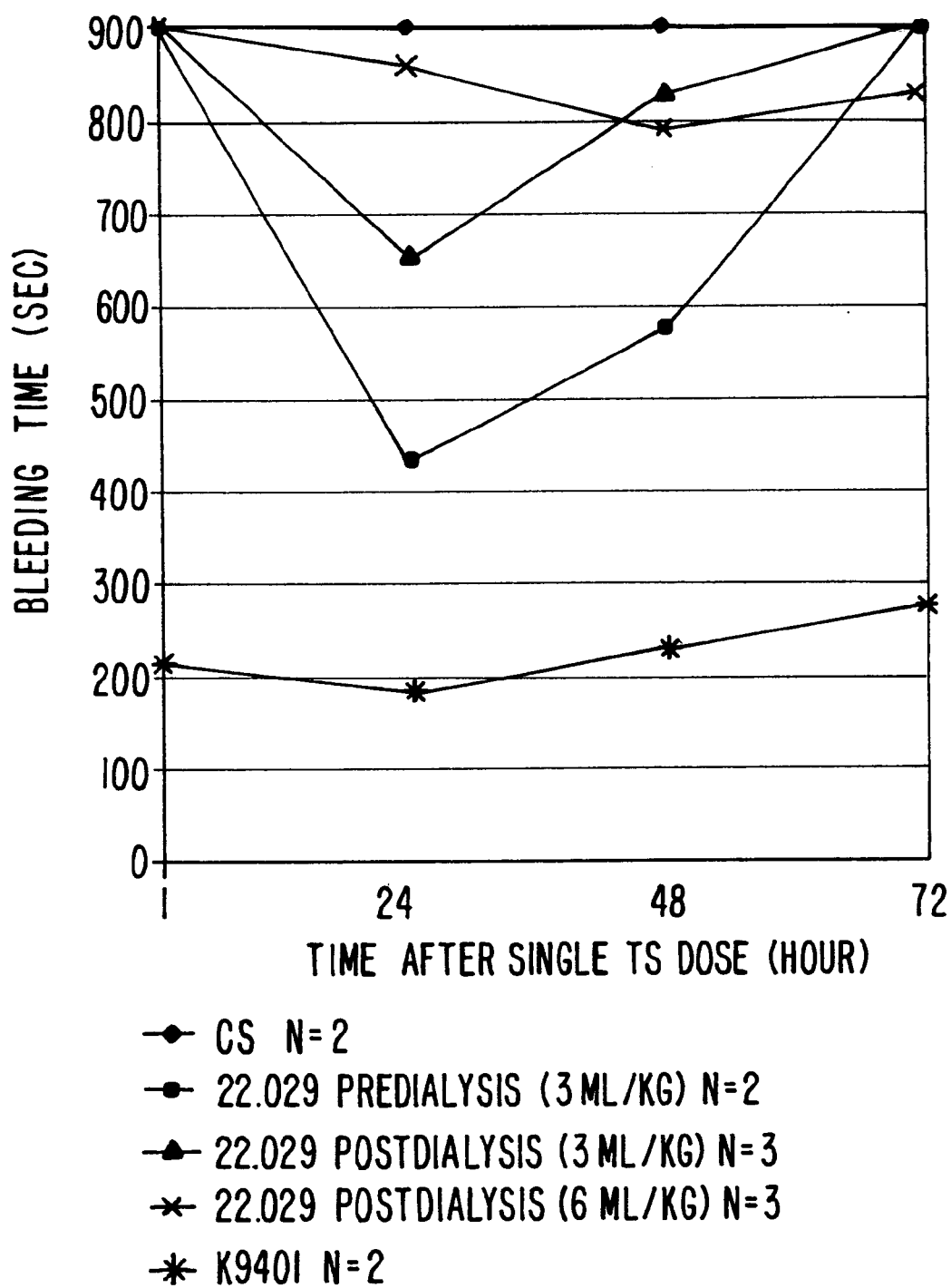
FIG. 6 shows the effect on bleeding time of TS2 in two stages of its preparation.

The effect of TS2 (Lot 22.029) in two stages of its preparation was tested. Samples of this lot after Membrex filtration and before the Asahi diafiltration ("Pre-dialysis") had moderate effects in improving the bleeding time of thrombocytopenic rabbits (FIG. 6). This effect correlates well with the concentration of FPA/$10^9$ TS (23 ng/$10^9$ TS.) However, even this effect became negligible after 72 hours post-dose. In contrast, samples of this lot after the diafiltration step ("Postdialysis") showed minimal effect on the bleeding time of severely thrombocytopenic rabbits. These ineffective spheres had 4.3 to 7.5 ng FPA/$10^9$ TS (Table 2).

TABLE 2

FPA (FIBRINOGEN) BALANCE DURING FILTRATION OF TS2

| Step | Volume (liter) | FPA (ng/ml) On Spheres | FPA (ng/ml) Super-natant | Total FPA (microgram) On Spheres | Total FPA (microgram) Super-natant |
|---|---|---|---|---|---|
| 1. Pre-Membrex Bulk | 2.47 | 353 | 160 | 872 | 395 |
| 2. Membrex retentate | 1.99 | 304 | 93 | 605 | 185 |
| 3. Pre-dialysis | 8.35 | 59 | 50 | 493 | 418 |
| 4. Dialysate | 12.0 | 15 | 49 | 180 | 588 |
| 5. Final product | 2.2 | 12 | 24 | 26 | 53 |

B. Hemostatic Function of TS1 and TS3

Tables 3–8 summarize experiments determining the effect of administration of TS3 on bleeding time of thrombocytopenic rabbits. "PC" is platelet count (platelets×$10^3$ per milliliter) and "BT" refers to bleeding time in seconds (3 digit number) or minutes (>15, >30, >60).

Tables 3 and 4 summarize the results with two different doses of TS3 (Lot 22.038). (Table 3=6.0 ml/Kg at 3×$10^9$ TS3/ml; Table 4=10 ml/Kg at 3×$10^9$ TS3/ml). The higher dose of TS3 (10 ml/Kg) (Table 4) had better hemostatic fuinction. The antithrombo-cytopenic effect persists for at least 72 hours.

Table 5 shows the results with the supernatant from TS3 (Lot 22.038), which did not correct the bleeding times in thrombocytopenic rabbits. Table 6 shows data from 6 control rabbits which were injected with normal saline.

Tables 7 and 8 show results obtained in experiments with TS3 (Table 7) (rabbits injected with 10.0 ml/Kg TS3 lot 22.033@ 1.6×$10^9$ TS3/ml) and TS1 (rabbits injected with 3.0 ml/Kg TS1 lot 49.401@ 3.0×$10^9$ TS/ml) (Table 8). In this experiment, the bleeding times were done at 2, 4, 5 and 7 days post-infusion. The effect of these fibrinogen-coated microspheres persists for approximately 5 days (120 Hours) with both TS1 and TS3. In these experiments the rabbits were irradiated on day 0, with the platelet antiserum and TS3 or TS1 infused 4 days later. For the 7-day (144-hour) hemostatic function experiments, platelet antiserum had to be given prior to the bleeding time determinations being done, as the residual platelet counts were in the 50×$10^9$/ range.

Some of the hemostatic function observed on day 5 (120 hours) may relate, in part, to the presence of young platelets in the circulation. However, the hemostatic effect through 72 hours (and probably through 96 hours) are not accounted for by the appearance of young platelets.

TABLE 3

EFFECT OF A SECOND DOSE OF TS3 TO THROMBOCYTOPENIC RABBIT

| Rabbit | One hour* Plt Ct# | One hour* BT | 24 hour* Plt Ct | 24 hour* BT | 48 hour Plt Ct | 48 hour BT | 72 hour Plt Ct | 72 hour BT |
|---|---|---|---|---|---|---|---|---|
| 1 | 5 | >900 | 3 | >900 | 4 | 362 | 5 | 268 |
| 2 | 5 | >900 | 4 | >900 | 5 | 445 | 6 | 298 |
| 3 | 4 | >900 | 6 | >900 | 7 | 360 | 8 | 262 |

*First dose (9 × $10^9$ TS3, Lot 22.038) was infused i.v. at 0 hour. repeat dose (9 ×$10^9$ TS3, Lot 22.038) was infused i.v. immediately after 24 hour bleeding time (BT) measurement.
Plt Ct = platelet count. × $10^3/\mu l$

TABLE 4

SPH # 34 + 35

| RAB # | PC 24 Hrs | BT 24 Hrs | BT MEAN 24 Hrs | PC 72 HRS | BT 72 HRS | BT MEAN 72 HRS |
|---|---|---|---|---|---|---|
|  |  | 690 |  |  | 703 |  |
| R1 | 5 | 456 | 573 | 5 | 647 | 675 |
|  |  | 961 |  |  |  |  |
| R2 | 6 | 789 | 875 | 6 | >30 | >30 |
|  |  | 612 |  |  | 711 |  |
| R3 | 7 | 643 | 628 | 7 | 719 | 715 |
|  |  | 896 |  |  | 941 |  |
| R13 | 2 | 942 | 919 | 3 | 874 | 908 |
|  |  | 861 |  |  | 893 |  |
| R14 | 3 | 897 | 879 | 4 | 963 | 928 |
|  |  | 703 |  |  | 1112 |  |
| R15 | 4 | 694 | 699 | 3 | 997 | 1055 |
| MEAN | 5 |  | 762 | 5 |  | 856 |
| SD +− | 1.9 |  | 148 | 1.6 |  | 158 |
| MEDIAN | 5 |  | 787 | 5 |  | 908 |

Rabbits # 1–3 + 13–15 Injected with 6.0 ml\Kg S22-038 @ 3.0 × 10^9 TS/ml

TABLE 5

| RAB # | PC 24 Hrs | BT 24 Hrs | BT MEAN 24 Hrs | PC 72 HRS | BT 72 HRS | BT MEAN 72 HRS |
|---|---|---|---|---|---|---|
|  |  | 307 |  |  | 426 |  |
| R4 | 7 | 422 | 365 | 9 | 481 | 454 |
|  |  | 420 |  |  | 357 |  |
| R5 | 6 | 481 | 451 | 7 | 464 | 411 |
|  |  | 450 |  |  | 439 |  |
| R6 | 6 | 412 | 431 | 7 | 403 | 421 |
|  |  | 521 |  |  | 482 |  |
| R16 | 4 | 489 | 505 | 5 | 543 | 513 |
|  |  | 549 |  |  | 333 |  |
| R17 | 5 | 524 | 537 | 8 | 401 | 367 |
|  |  | 619 |  |  | 610 |  |
| R18 | 4 | 624 | 622 | 3 | 701 | 656 |
| MEAN | 5 |  | 485 | 7 |  | 470 |
| SD +− | 1.2 |  | 90 | 2.2 |  | 103 |
| MEDIAN | 6 |  | 478 | 7 |  | 437 |

Rabbits # 4–6 + 16–18 Injected with 10.0 ml\Kg S22-038 @ 3.0 × 10^9 TS/ml

TABLE 6

SPH # 34 + 35

| RAB # | PC 24 Hrs | BT 24 Hrs | BT MEAN 24 Hrs | PC 72 HRS | BT 72 HRS | BT MEAN 72 HRS |
|---|---|---|---|---|---|---|
| R7 | 7 | >60 | >60 | 8 | >60 | >60 |
| R8 | 8 | >30 | >30 | 7 | >60 | >60 |
| R9 | 9 | >30 | >30 | 8 | >90 | >90 |
| R19 | 4 | >30 | >30 | 5 | >60 | >60 |
| R20 | 3 | >30 | >30 | 4 | >60 | >60 |
| R21 | 4 | >30 | >30 | 5 | >60 | >60 |
| MEAN | 6 |  | >30 | 6 |  | >60 |
| SD +− | 2.5 |  |  | 1.7 |  |  |
| MEDIAN | 6 |  |  | 6 |  |  |

Rabbits # 7–9 + 19–21 Injected with 10.0 ml\Kg S22-038 @ 3.0 × 10^9 TS/ml SUPERNATANT

TABLE 7

| RAB # | PC 24 Hrs | BT 24 Hrs | BT MEAN 24 Hrs | Pc 72 HRS | BT 72 HRS | BT MEAN 72 HRS |
|---|---|---|---|---|---|---|
| R10 | 8 | >30 | >30 | 6 | >90 | >90 |
| R11 | 8 | >30 | >30 | 8 | >60 | >60 |
| R12 | 6 | >30 | >30 | 9 | >60 | >60 |
| R22 | 3 | >30 | >30 | 4 | >60 | >60 |
| R23 | 4 | >30 | >30 | 6 | >60 | >60 |
| R24 | 3 | >30 | >30 | 5 | >60 | >60 |
| MEAN | 5 | | >30 | 6 | | >60 |
| SD +− | 2.3 | | | 1.9 | | |
| MEDIAN | 5 | | | 6 | | |

Rabbits # 10–12 + 22–24 Injected with 10.0 ml\Kg NORMAL SALINE

TABLE 8

Rabbits #7–10 + 13–14 Injected with 10.0 ml\Kg S22-033 @ 1.6 × 10$^9$ TS/ml

| RAB # | PC 48 Hrs | BT 48 Hrs | BT MEAN 48 Hrs | PC 96 Hrs | BT 96 Hrs | BT MEAN 96 Hrs | PC 120 Hrs | BT 120 Hrs | BT MEAN 120 Hrs | PC 144 Hrs | BT 144 Hrs | BT MEAN 144 Hrs |
|---|---|---|---|---|---|---|---|---|---|---|---|---|
| R7 | 8 | 487 510 | 499 | 10 | 467 493 | 480 | 12 | 488 502 | 495 | 10 | >15 min | >15 min |
| R8 | 7 | 501 462 | 482 | 9 | 610 549 | 580 | 6 | 594 528 | 561 | 12 | >15 min | >15 min |
| R9 | 9 | 481 463 | 472 | 10 | 427 483 | 455 | 15 | 301 490 | 396 | 14 | >15 min | >15 min |
| R10 | 9 | 383 401 | 392 | 11 | 427 491 | 459 | 9 | 610 924 | 767 | 11 | >15 min | >15 min |
| R13 | 8 | 407 385 | 396 | ND | ND | ND | 7 | 501 439 | 470 | ND | ND | ND |
| R14 | 9 | 399 421 | 410 | ND | ND | ND | 8 | 473 461 | 467 | ND | ND | ND |
| MEAN | 8 | | 442 | 10 | | 493 | 10 | | 526 | 12 | | >15 min |
| SD+− | 0.8 | | 475 | 0.8 | | 58.5 | 3.4 | | 129.5 | 1.7 | | |
| MEDIAN | 9 | | 441 | 10 | | 470 | 9 | | 483 | 12 | | |

C. Reduction in Blood Loss

Figure 7A:
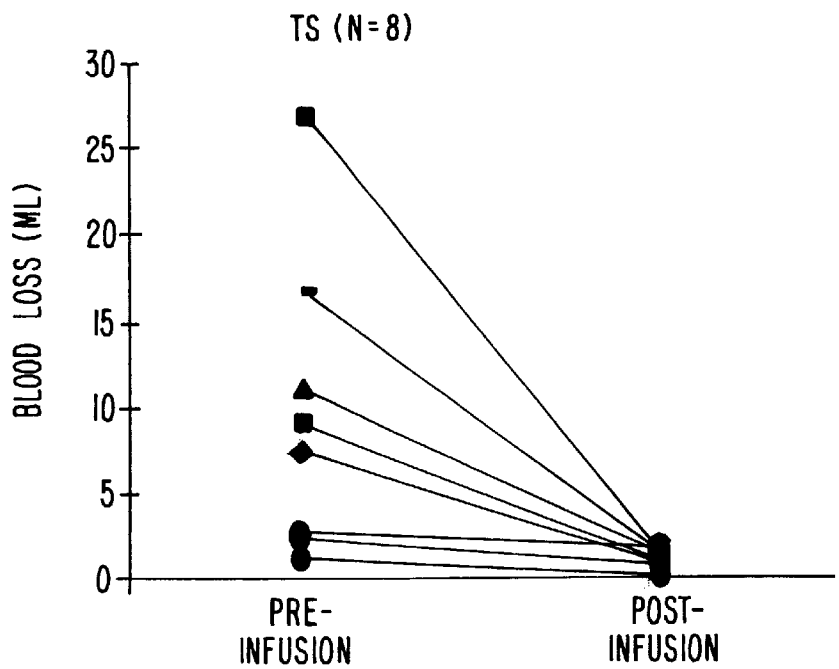
FIG. 7 shows reduction of blood loss by TS1 in thrombocytopenic rabbits.
Figure 7B:
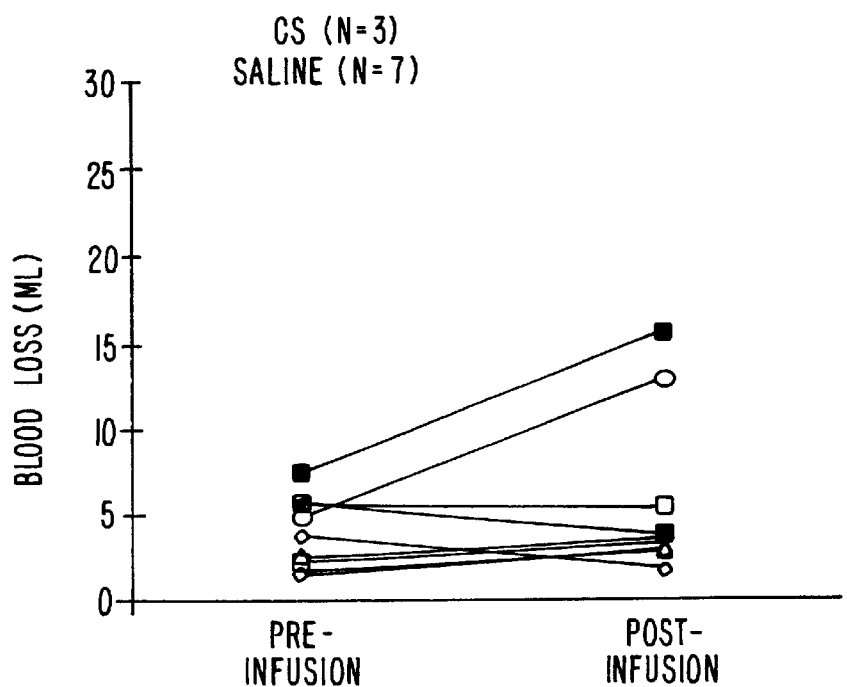

Experiments with TS1 also demonstrate efficacy in reducing the amount of blood loss in thrombocytopenic rabbits. FIG. 7 shows that although the volume of blood loss varied greatly initially among these rabbits, reduction in blood loss was obvious after an infusion of 7.5×10$^9$ TS1/kg (Lot K9401). CS and normal saline controls showed no improvements in the amount of blood loss.

D. Effect of Repeat Dose

The effect of a repeat dose of TS3 (Lot 22.038) on severely thrombocytopenic rabbits is shown in Table 9. Previous results demonstrated that a single dose of 9×10$^9$ TS3/kg was minimally effective in improving the bleeding time. It was surprising to note that a second dose of 9×10$^9$ TS3/kg infused at 24 hours resulted in bleeding-times shorter than one dose of 90×10$^9$ TS3/kg after 48 and 72 hours (see FIG. 5). The mechanism underlying this observation is not clear. One possibility is that the second dose preferentially affects the less-than-one-day old platelets that appear after administration of the first dose.

TABLE 9

Rabbits #1–6 + 11–12 Injected with 3.0 ml\Kg K9401 @ 3.0 × 10$^9$ TS/ml

| RAB # | PC 48 Hrs | BT 48 Hrs | BT MEAN 48 Hrs | PC 96 Hrs | BT 96 Hrs | BT MEAN 96 Hrs | PC 120 Hrs | BT 120 Hrs | BT MEAN 120 Hrs | PC 144 Hrs | BT 144 Hrs | BT MEAN 144 Hrs |
|---|---|---|---|---|---|---|---|---|---|---|---|---|
| R1 | 10 | 193 295 | 244 | 8 | 326 243 | 285 | 10 | 403 319 | 381 | 9 | >15 min | >15 min |
| R2 | 9 | 245 280 | 263 | 8 | 301 273 | | | 384 314 | 439 | 14 | >15 min | >15 min |
| R3 | 6 | 279 369 | 324 | 7 | 319 341 | 330 | 8 | 327 351 | 339 | 3 | >15 min | >15 min |
| R4 | 7 | 258 281 | 270 | 7 | 278 299 | 289 | 7 | 410 396 | 403 | 15 | >15 min | >15 min |
| R5 | 8 | 278 | 281 | 9 | 258 | 280 | 10 | 540 | 543 | 13 | 891 | >15 min |

TABLE 9-continued

Rabbits #1–6 + 11–12 Injected with 3.0 ml\Kg K9401 @ 3.0 × 10^9 TS/ml

| RAB # | PC 48 Hrs | BT 48 Hrs | BT MEAN 48 Hrs | PC 96 Hrs | BT 96 Hrs | BT MEAN 96 Hrs | PC 120 Hrs | BT 120 Hrs | BT MEAN 120 Hrs | PC 144 Hrs | BT 144 Hrs | BT MEAN 144 Hrs |
|---|---|---|---|---|---|---|---|---|---|---|---|---|
|  |  | 284 |  |  | 301 |  |  | 546 |  |  | >15 min |  |
| R6 | 9 | 299 | 302 | 10 | 327 | 336 | 9 | 356 | 345 | 2 | >15 min | >15 min |
|  |  | 304 |  |  | 344 |  |  | 333 |  |  |  |  |
| R11 | 7 | 278 | 269 | ND | ND | ND | 8 | 37 | 365 | ND | ND | ND |
|  |  | 259 |  |  |  |  |  | 342 |  |  |  |  |
| R12 | 8 | 301 | 274 | ND | ND | ND | 6 | 318 | 329 | ND | ND | ND |
|  |  | 246 |  |  |  |  |  | 339 |  |  |  |  |
| MEAN | 8 |  | 278 | 8 |  | 301 | 8 |  | 379 | 9 |  | >15 min |
| SD+− | 1 |  | 25 | 1 |  | 25 | 1 |  | 70 | 6 |  |  |
| MEDIAN | 8 |  | 272 | 8 |  | 288 | 8 |  | 355 | 11 |  |  |

Safety

A. Thrombogenic Potential

The thrombogenic potential of TS preparations was tested. High doses of TS1 (K9401) and TS3 (Lot 22.038) were infused in the right internal jugular vein of anesthetized rabbits and followed using the Wessler model (Wessler et al., 1959, *J. Appl Physiol.* 14:943–6) to check for blood clots in the left internal jugular vein. Essentially, 20 male rabbits weighing 2.5–2.8 kg were divided into four groups each containing five rabbits. The groups were respectively administered vehicle (0.9% saline), TS1 at 1 mL(=2.5×10$^9$)/kg, or TS1 at 8 mL(=24×10$^9$)/kg, and thromboplastin at 1 mg/rabbit (as a positive control). No thrombus was observed in any of the left (stasis-induced) jugular veins, in TS treated rabbits. In contrast, the administration of thromboplastin was associated with thrombus formation in both the left and right jugular veins.

B. Acute Toxicity (Single Dose)

1. TS1

The doses used for the study of TS1 (Lot K9401) were 0.84, 4.2 and 14.0 mL/kg for the low, mid, and high doses respectively, which represented doses of 2.1, 10.5 and 35×10$^9$ TS/kg, respectively. There were no clinical signs observed during the acute single dose intravenous toxicity study. There were no statistically significant difference in body weight for any test group when compared to control. None of the animals died. Clinical laboratory values were normal.

2. TS3

For TS3 (Lot 22.038), the low, medium, high doses were: 3.3 mL/kg, 10 mL/kg, 8.3 mL/kg (a 4× greater concentration) which represented doses of 10, 30 and 100× 10$^9$ TS/kg, respectively. Control solution was normal saline given at 10 mL/kg. Signs of increased respiration were observed in two high dose animals during dosing. No other clinical signs were observed during the study. There were no statistically significant differences in body weigh for any test group when compared to controls. None of the animals died during the study. Pale kidneys were observed in all animals at terminal necropsy (normally associated with terminal bleeding). Fibrin degradation product (FDP) was observed in one female in the medium dose at one hour and in all high dose animals at 1 and 4 hours (possibly due to (human) fibrin in reconstituted samples of Lot 22.038). Except for the high FDP values in these animals, all the coagulation parameters in all the animals were normal and there were no signs of disseminated intravascular coagulation.

C. Serotonin release

Compared to saline, TS1 (Lot K9401) in a concentration of 1×10$^8$ TS/mL augmented $^{14}$C-serotonin release from platelets activated by agonists at concentrations that normally caused sub-maximal release. However, in the absence of platelet agonists, TS caused no serotonin release. TS1 at the concentration of 2.5×10$^8$/mL had no effect on the PT, PTT or TCT of plasma from patients anticoagulated with coumadin or heparin. The presence of TS augments agonist-induced platelet activation and aggregation, but TS1 did not by itself cause platelet aggregation in vitro.

Pharmacokinetics

The pharmacokinetics of $^{125}$I-labeled TS1 was evaluated as follows:

1. Radiochemical Purity and Stability of $^{125}$I-labeled TS1

The radiochemical purity of $^{125}$I-labeled TS1 was greater than 95% and often approached 100% as determined by paper chromatography. The radiochemical purity of $^{125}$I-labeled TS1 was maintained for at least 30 days when stored at 4° C. Furthermore, no $^{125}$I radioactivity was found in the supernatants of serial blood samples taken from rabbits infused with $^{125}$I-labeled TS1. Thus, there was no evidence of in vitro or in vivo label instability for $^{125}$I-labeled TS1.

2. In vivo Efficacy of $^{125}$I-labeled TS1

Similar to the non-labeled starting material, $^{125}$I-labeled TS1 shortened the ear bleeding time in two thrombocytopenic rabbits with platelet counts of <10×10$^3$/μL. One rabbit had a bleeding time of 422 and 355 seconds at 1 and 78 hours post-dose, respectively. A second rabbit had a bleeding time of 409 and 424 seconds at 1 and 78 hours post-dose, respectively. Thus, there was no evidence that the $^{125}$I-labeling process altered the in vivo hemostatic efficacy of TS.

3. Recovery of $^{125}$I from the Circulation of Rabbits Infused with $^{125}$I-labeled TS1

Figure 8:
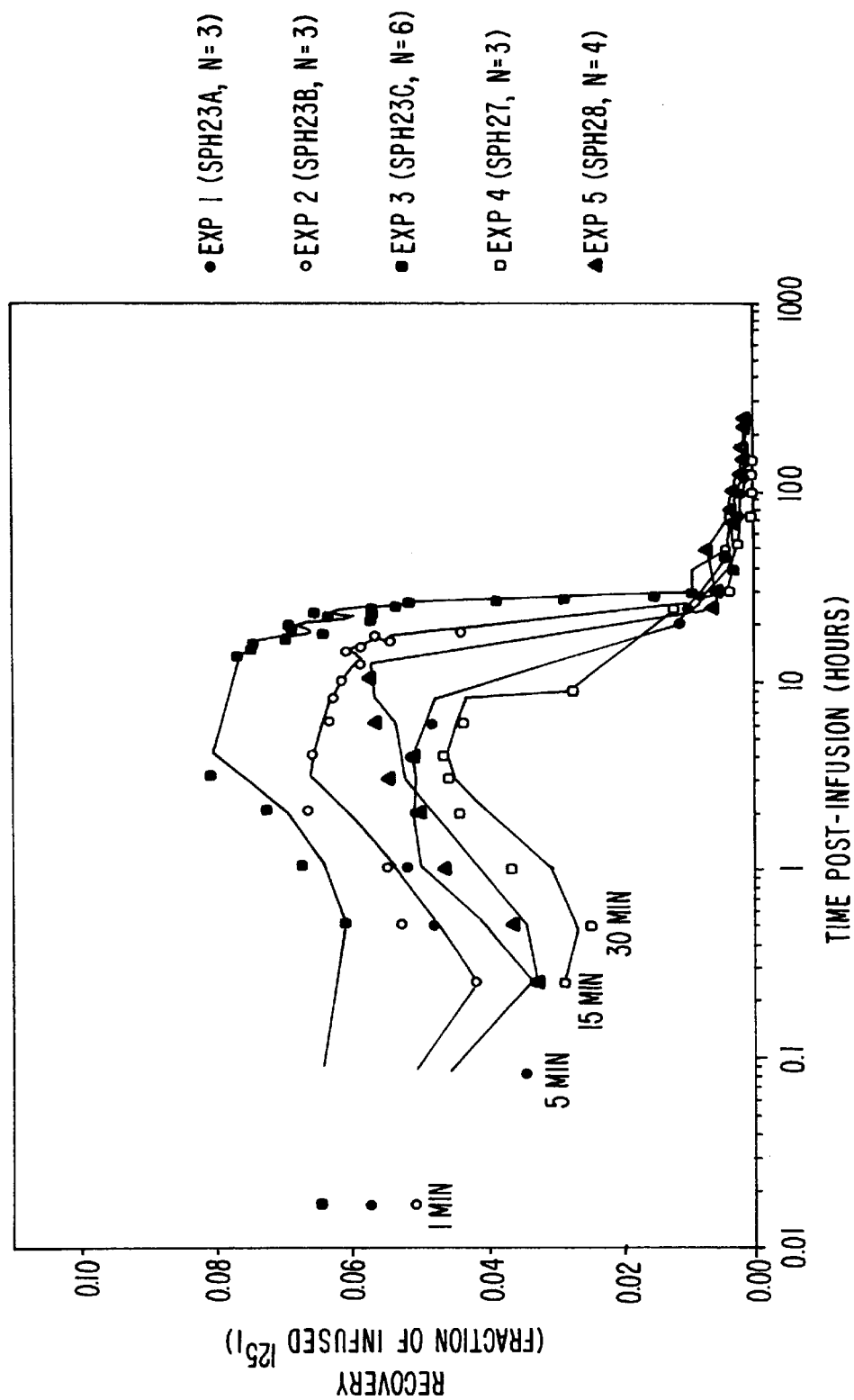
FIG. 8 shows recovery of TS1 from circulation.

After a single bolus infusion of 7.5×10$^9$ $^{125}$I-labeled TS1kg, the pattern of recovery of $^{125}$I from the circulation was complex but consistently reproducible between experiments. This is summarized for the 5 experiments in FIG. 8. The pattern of $^{125}$I recovery from circulation was similar for normal rabbits (n=15) and thrombocytopenic rabbits (n=4.)

There was an immediate initial clearance of the vast majority of the $^{125}$I-labeled TS1 , resulting in a recovery in blood of 5% to 7%, 1 minute post-infusion. By 30 minutes, 2% to 6% was recoverable. Thereafter, the circulating $^{125}$I increased to 4% to 8% between 1 and 3 hours post-infusion. Over the next several hours the circulating $^{125}$I level decreased only slightly, until there was a rapid decline occurring between 20 and 30 hours post-infusion. $^{125}$I recovery at 30 hours was less than 1%, and continued to decrease beyond 30 hours.

4. Elimination of $^{125}$I from Rabbits Infused with $^{125}$I-labeled TS1

Figure 9:
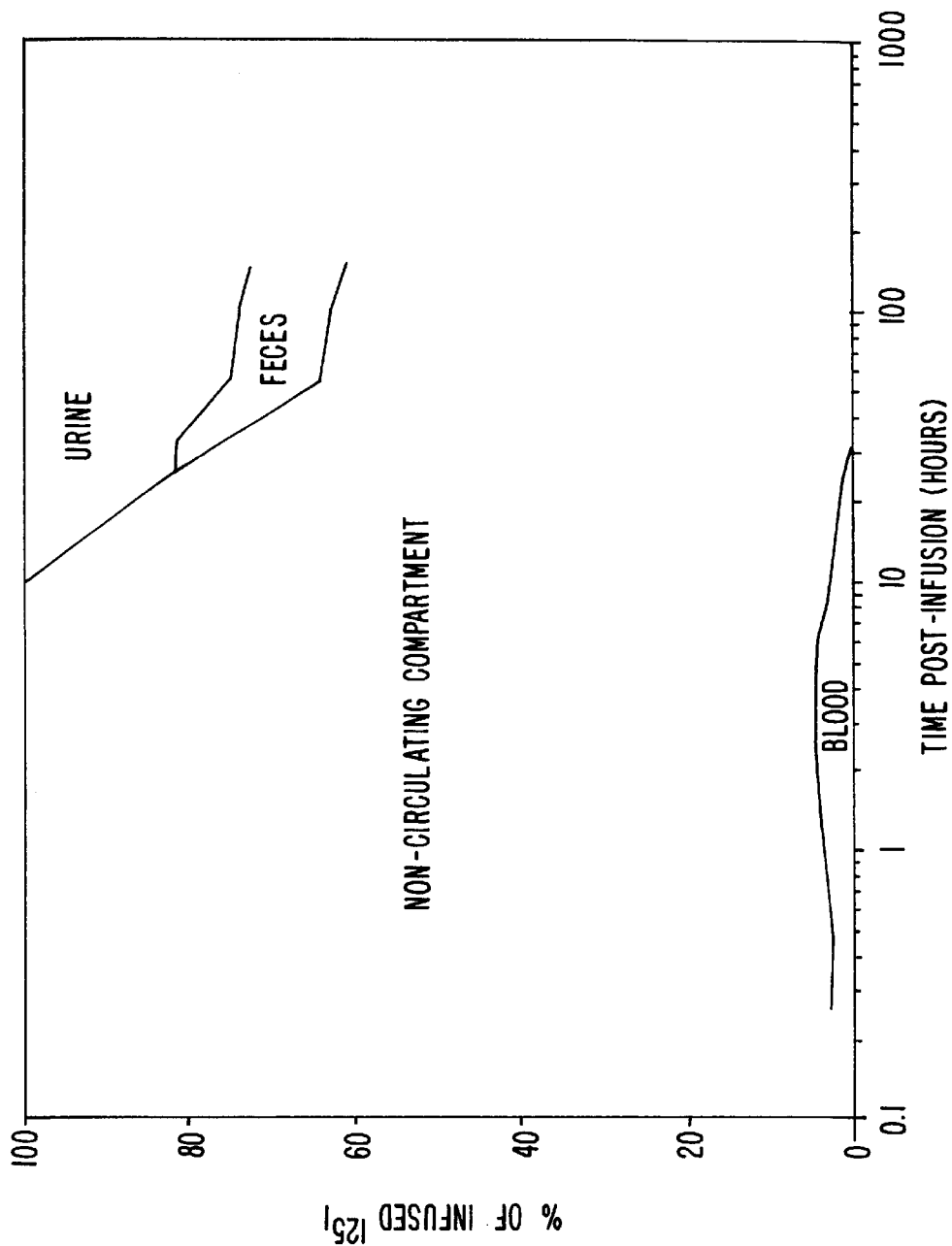
FIG. 9 shows elimination of infused TS1 in normal rabbits.

The $^{125}$I radioactivity was measured in the urine and feces of 3 normal rabbits and 4 thrombocytopenic rabbits infused with $^{125}$I-labeled TS1. The mean results for excreted and blood $^{125}$I radioactivity for 3 normal rabbits was shown in FIG. 9. Forty percent of the infused $^{125}$I was excreted in urine and feces by 100 hours. Any of the infused $^{125}$I radioactivity that was not accounted for in blood, urine, or feces must reside in a non-circulating compartment. At 100 hours, 60% of the infused $^{125}$I was unaccounted for by blood, urine, and feces; therefore it resided in the non-circulating compartment. Of the excreted radioactivity, most of it was excreted in the urine.

Figure 10:
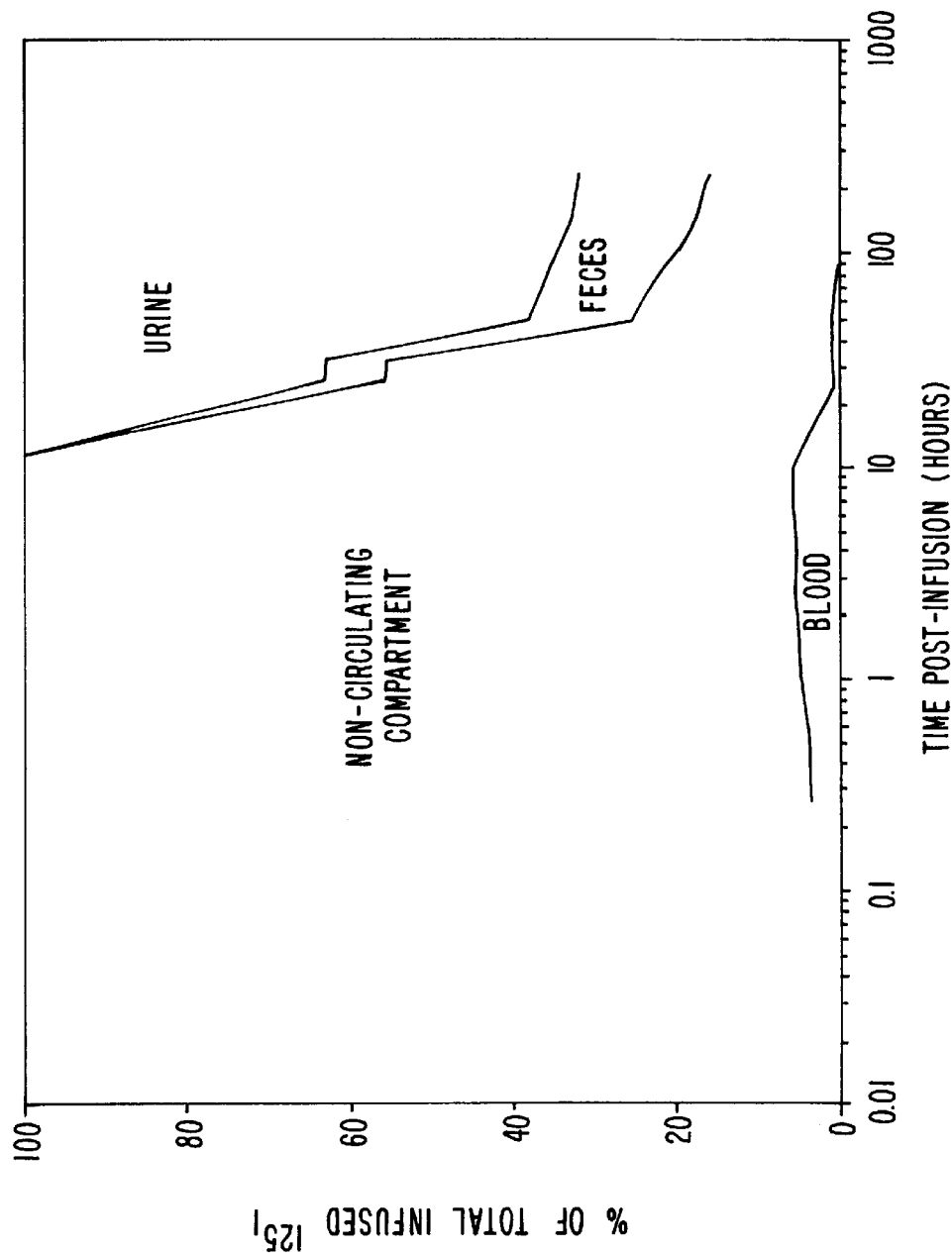
FIG. 10 shows elimination of infused TS1 in thrombocytopenic rabbits.

For thrombocytopenic rabbits, a similar pattern of elimination was seen but a greater proportion of the overall radioactivity was excreted, primarily in the urine (FIG. 10). On the average, 16% of the infused $^{125}$I still resided in the non-circulating compartment 243 hours post-infusion. The raw data in this experiment had greater variation than that in FIG. 9.

5. Organ distribution of $^{125}$I After Infusion of $^{125}$I-labeled TS1

The 4 thrombocytopenic rabbits were sacrificed at 243 hours. The radioactivity in the spleen, heart, kidneys, lungs, and liver accounted for only 0.2% of -the infused $^{125}$I. The weight of these organs collectively accounted for approximately 5% of the rabbit. The percentage of the total infused $^{125}$I that was retrievable from each organ, expressed per organ and expressed per gram of each organ is shown in Table 10.

TABLE 10

ORGAN DISTRIBUTION OF $^{125}$I FROM INFUSED $^{125}$I-LABELED TS1

| Organ | % of total infused $^{125}$I per whole organ | % of total infused $^{125}$I per gram of organ |
| --- | --- | --- |
| spleen | 0.005 | 0.0025 |
| heart | 0.002 | 0.0003 |
| kidneys | 0.020 | 0.0009 |
| lungs | 0.042 | 0.0026 |
| liver | 0.118 | 0.0011 |

Particle Size and Filtration

A. Effect of Filtration on Size Distribution

The effectiveness of filtration in removing particles larger than 3 or 5 micron was evaluated. FIG. 11 shows the particle size difference between TS1 and TS3 as observed with light microscopy with a 100× magnification (the cross bar=7 micron).

Figure 11A:
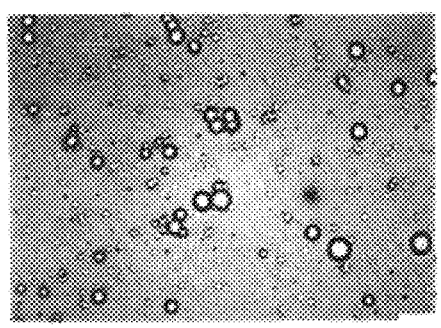
FIG. 11A–H shows the effect of filtration on removing particles.

TS1 (Lot K9401, reconstituted suspension from lyophilized powder) contained many particles (single spheres or aggregates) with diameter larger than 7 micron (FIG. 11A). Spheres smaller than 1 micron were difficult to discern with this magnification under the light microscope.

TS3 (Lot 22.033) contained no large aggregates. A few particles approximately 7 micron in diameter could be seen even though a "3 micron" filter had been used (FIG. 11H), suggesting that the filter "pore size" was not absolute. In experiments with TS3 (Lot 22.038) there was no evidence of cross-linking of spheres due to addition of the second dose of glutaraldehyde. Prior to the Membrex filtration step (FIG. 11F) this lot contained numerous large particles. However, after the Membrex filtration, diafiltration with the Asahi apparatus, lyophilization, and reconstitution with normal saline, the final suspension showed none of the large spheres (FIG. 11G) This showed that a second dose of crosslinking agent (to effect the binding of fibrinogen to the spheres) does not by itself cause aggregation of spheres.

Figure 11E:
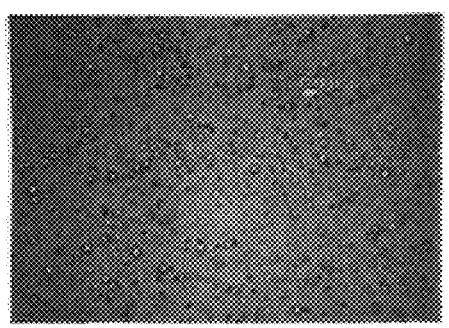
Figure 11B:
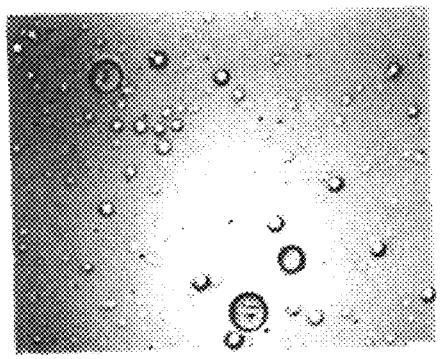
Figure 11F:
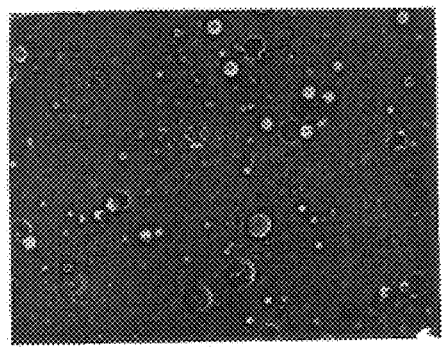
Figure 11C:
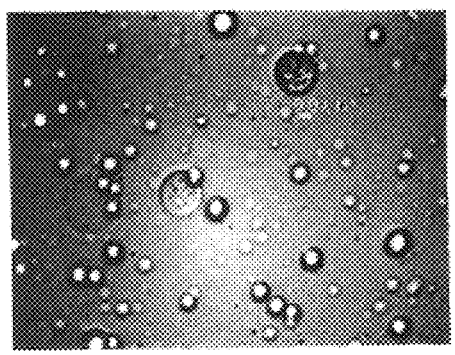
Figure 11G:
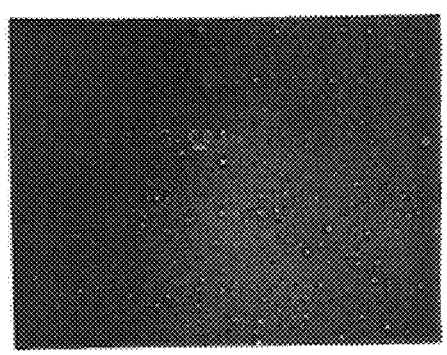
Figure 11D:
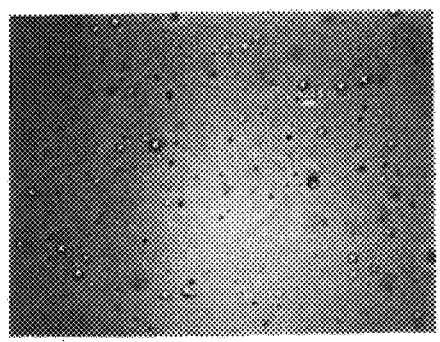
Figure 11H:
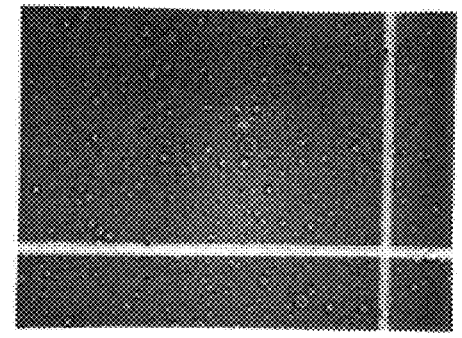
Figure 12A:
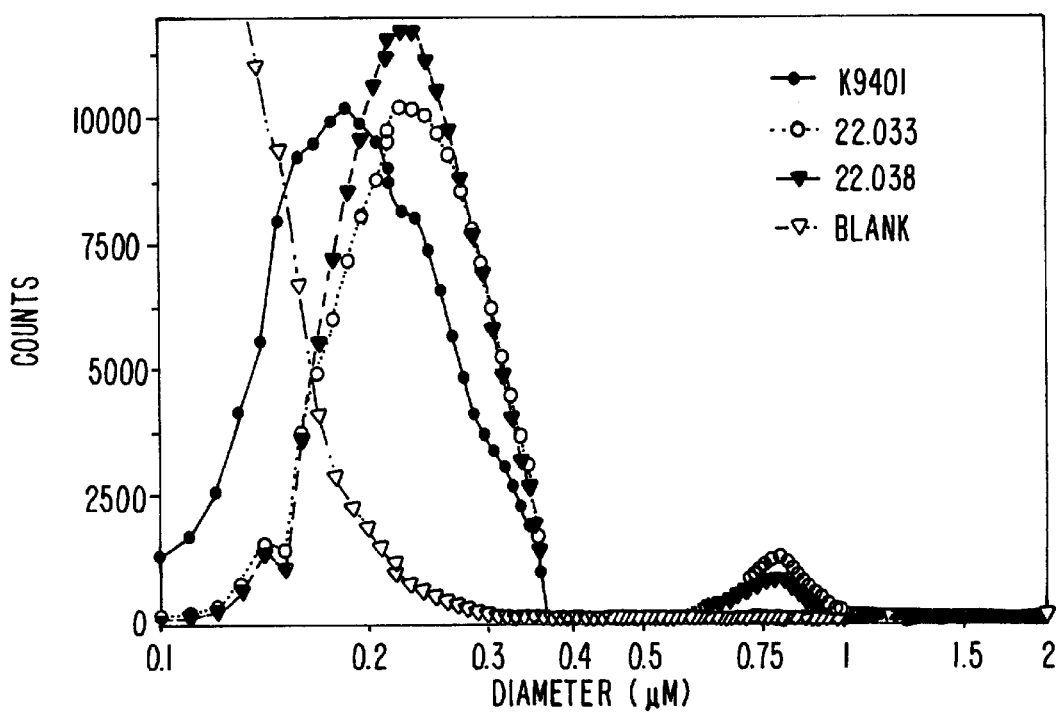
FIG. 12A–D shows the distribution of sphere sizes in reconstituted suspensions as determined using the HIAC particle counter.
Figure 12B:
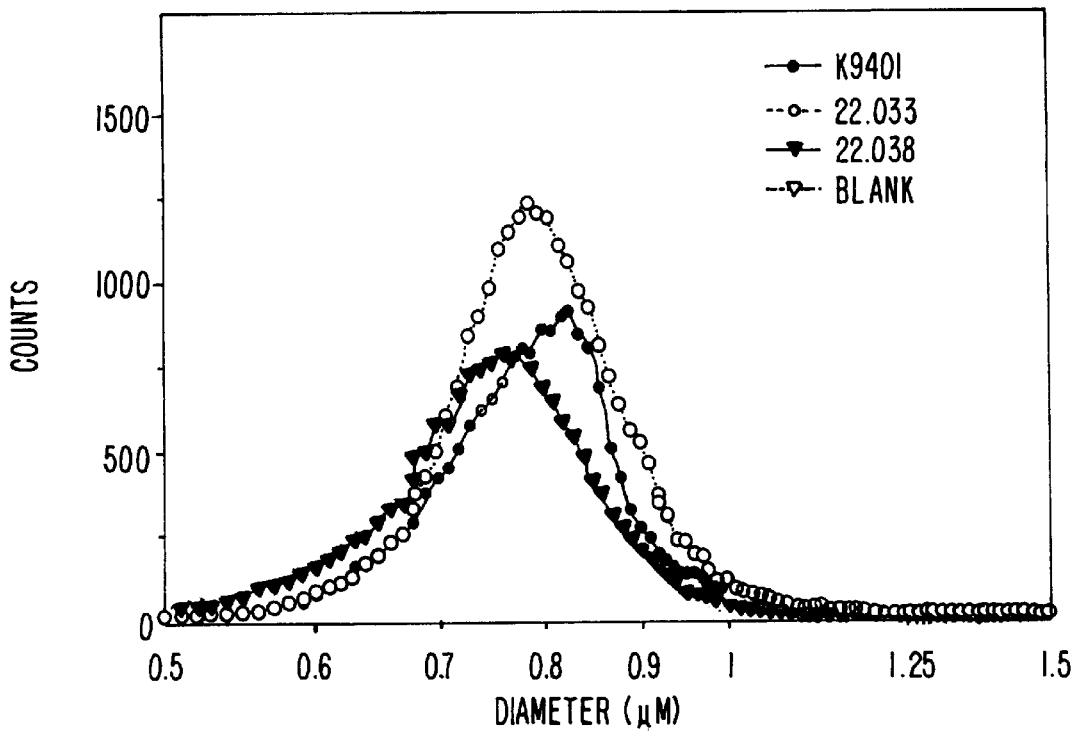
Figure 12C:
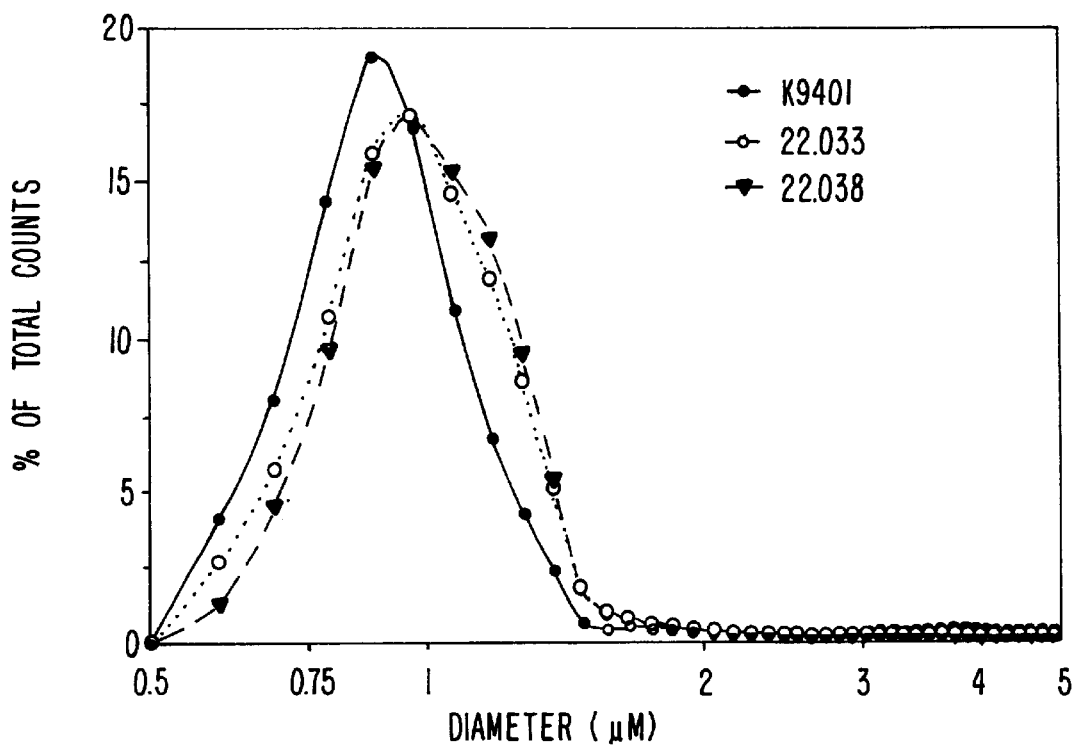
Figure 12D:
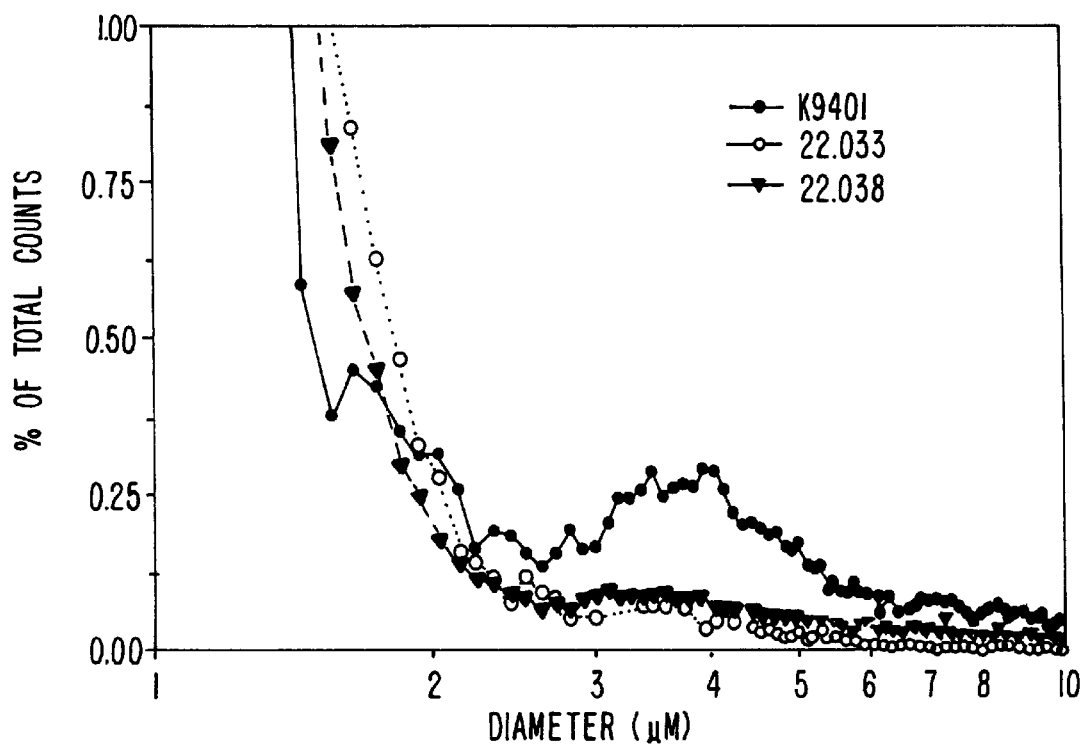

TS2 (Lot 22.026) was also studied. FIGS. 11B, C, D, E show the bulk suspension before Membrex filtration, retentate of the Membrex system, filtrate from the Membrex filter before diafiltration, and liquid suspension of the same filtrate after diafiltration in the Asahi cartridge, respectively, taken under similar condition. It was apparent that the retentate in the Membrex system had far fewer small spheres (FIG. 11C) compared to that in the pre-Membrex suspension (FIG. 11B.) All the large particles were removed by filtration (FIG. 11D.) The concentration of small spheres (average size 3 micron easily captured in the photograph) were increased by diafiltration (FIG. 11E.)

CS (not shown) looked like Lot K9401, i.e., many large spheres were present.

FIG. 12 shows the distribution of sphere sizes in reconstituted suspensions as determined using the HIAC particle counter. Most noticeably, reconstituted suspensions of TS1 (Lot K9401) and TS3 (Lots 22.033 and 22.038) had a large population of spheres about 0.2 to 0.3 micron in diameter (FIG. 12A) which was not detected with the Coulter Multisizer II. These small spheres were about 7 times as populous as the 0.8 micron spheres. FIG. 12B showed the amplified distribution of the spheres with average diameter of 0.8 micron. FIG. 12C expressed the concentration of the 0.8 spheres as a percentage of the entire sphere population. FIG. 12D confirmed that TS1 (Lot K9401) had a population of sphere about 4 micron in diameter which was about 0.25% of the entire sphere population, which was essentially absent in TS3 (Lots 22.033 and 22.038). The HIAC counter was not used to evaluate the concentration of spheres or particles substantially larger than 5 micron.

Table 11 shows the effect of filtration on sphere sizes. By visually inspecting the suspensions in the hemocytometer, single large spheres could be distinguished from aggregates. After taking pictures with the video camera, the relative size of the particles could be compared to a reference crossbar of 7 micron.

TABLE 11

TABLE 1: EFFECT OF FILTRATION ON SPHERE SIZE AND CONCENTRATION (10$_6$/ml) IN TS SUSPENSIONS

| Samples | Spheres (microns) | | | Aggregates (microns) | | |
| --- | --- | --- | --- | --- | --- | --- |
| | 7–10 | 10–25 | >25 | 7–10 | 10–25 | >25 |
| A. Lot K9401 | | | | | | |
| 1. Lyophilized, reconstituted | 2.4 | 6.0 | .25 | .14 | .80 | .26 |
| B. Lot 22.026 | | | | | | |
| 1. Pre-Membrex | 20 | 24 | 1 | 0 | 0 | 0 |
| 2. Membrex retentate | 19 | 33 | 2.9 | 0 | 0 | 0 |
| 3. Post-Membrex, predialysis | 0 | 0 | 0 | 0 | 0 | 0 |
| 4. Post-dialysis, liquid* | 0 | 0 | 0 | .004 | 0 | 0 |
| 5. Post-dialysis, liquid** | 0 | 0 | 0 | 0 | 0 | 0 |
| 5. Post-lyophiliza-tion# | 0 | 0 | 0 | .18 | .25 | .05 |
| C. Lot 22.033 | | | | | | |
| 1. Membrex retentate | 46 | 80 | 8 | 0 | 0 | 0 |

TABLE 11-continued

TABLE 1: EFFECT OF FILTRATION ON SPHERE SIZE AND CONCENTRATION (10$_6$/ml) IN TS SUSPENSIONS

| Samples | Spheres (microns) | | | Aggregates (microns) | | |
|---|---|---|---|---|---|---|
| | 7–10 | 10–25 | >25 | 7–10 | 10–25 | >25 |
| 2. Post-Membrex, predialysis | .03 | 0 | 0 | 0 | .02 | 0 |
| 3. Post-dialysis | .13 | .01 | 0 | .03 | .06 | 0 |
| 4. Post-fibrinogen | .10 | 0 | 0 | .08 | .12 | 0 |
| 5. Formulated liquid | 0 | 0 | 0 | .04 | .05 | 0 |
| 6. Lyophilized, reconstituted | .004 | .008 | 0 | .11 | .16 | .02 |
| D. Lot 22.038 | | | | | | |
| 1. Lyophilized, reconstituted | .07 | .04 | .003 | .08 | .4 | .24 |

*Stored as liquid form in water 4 degree C. without excepient for 2 weeks, not lyophilized;
**similarly for 8 weeks, not lyophilized
Formulated in 0.1M arginine, 5 mM Citrate, 0.5 mM EDTA, 1% lactose, 1% maltose, and 0.01% Tween-80

The number of microspheres larger than 7 microns was reduced by 2 to 3 orders of magnitude by either the 3 (TS3 Lot 22.033) or 5 micron filter (TS2 Lot 22.026 and TS3 Lot 22.038.) Addition of glutaraldehyde and fibrinogen by themselves did not substantially cause aggregation of spheres (TS3 Lot 22.033 "Post-fibrinogen" step). The concentration of aggregates in the "Post-Membrex" step was comparable to that in the "Formulated liquid" step.

A small number of aggregates formed after storage in the liquid form in 4° C., whether or not excipient was added. Lyophilization in the absence of added excipient (in formulations in which HSA was removed dialysis) or residual HSA led to aggregation of spheres (data not shown); however, the presence of added excipient in lyophilized samples reduced this aggregation to low levels.

B. Fibrinogen Loss During Filtration of TS2

Since the FPA/mL as well as FPA/$10^9$TS values for TS2 were drastically decreased compared to TS1, the FPA/mL and the total amount of FPA (concentration multiplied by volume) on the spheres, as well as in the supernatant, were analyzed as an index of where fibrinogen was lost at each step of the Membrex filtration and Asahi diafiltration process. Table 2 shows that the concentration of sphere-associated FPA decreased from an average of 38 to 23 ng/$10^9$ spheres in the (post-Membrex) pre-dialysis step, while that of the retentate in the Membrex system rose to 108 ng/$10^9$ spheres. (This suggested that the amount of fibrinogen per sphere was far greater in the large particles than in the smaller ones.) During the Membrex filtration step, the concentration of FPA in the supernatant was also greater in the retentate fraction (93 ng/mL) than the Membrex filtrate fraction (50 ng/mL). This suggested that part of the fibrinogen content that was previously on the spheres might have detached and moved into the soluble fraction. The value of 1 ng/$10^9$TS in the Asahi retentate fraction was probably an underestimation of the true concentration of FPA on the spheres, since the reconstituted product has about 4.2 ng/$10^9$TS. However, even this value of 4.2 was substantially lower than the 23 ng/$10^9$TS found on the spheres before this Asahi diafiltration ("pre-dialysis") step. Measurement of the FPA/mL showed that the Asahi dialysate actually had a higher value (49 ng/mL) than that of the Asahi retentate (33 ng/mL.) When the volume of the respective fractions were considered, the total amount of FPA in the dialysate was about 8 times more in the dialysate fraction (588 mg) than in the retentate fraction. This showed that the majority of fibrinogen was not covalently bound to the spheres and that most of the FPA was lost during the Asahi concentration/diafiltration step.

Removal of Large Particles by Centrifugation

The effectiveness of centrifugation in a tabletop centrifuge (Model Marathon 21K from Fisher Scientific, with a 16 cm rotor holding 50 mL conical tubes) to remove large particles as compared to filtration was studied. It was found that with a relative centrifuge force of 4000 g (i.e., 4700 rpm), the centrifugation time was important (Table 12). For a suspension of TS1 (containing at least 80×$10^6$/mL of particles larger than 5 micron) centrifugation time of less than 15 seconds was effective in decreasing the concentration of such particles by 15-fold. When the centrifugation time was increased to 90 seconds, the concentration of these large particles was reduced to $10^4$/mL. Particles with diameter larger than 10 micron were completely removed by 30 seconds of centrifugation. The total number of spheres did not substantially change at this high centrifugal force for a centrifugation time of up to 180 seconds.

TABLE 12

REMOVAL OF LARGE PARTICLES BY CENTRIFUGATION

| Centrifugation Time (sec) | # Samples | Total TS (× $10^9$/mL) | >10 μm TS (× $10^9$/mL) | >5 μm TS (× $10^9$/mL) |
|---|---|---|---|---|
| 0 | 2 | 7.62 | 6.48 | 86.2 |
| 15 | 4 | 7.37 | 0.168 | 5.56 |
| 30 | 4 | 7.82 | 16.65 | 3.63 |
| 60 | 4 | 8.46 | 0 | 0.36 |
| 90 | 4 | 8.19 | 0 | 0.01 |
| 180 | 4 | 6.91 | 0 | 0 |

Aggregation of Platelets and Microspheres

Figure 13A:
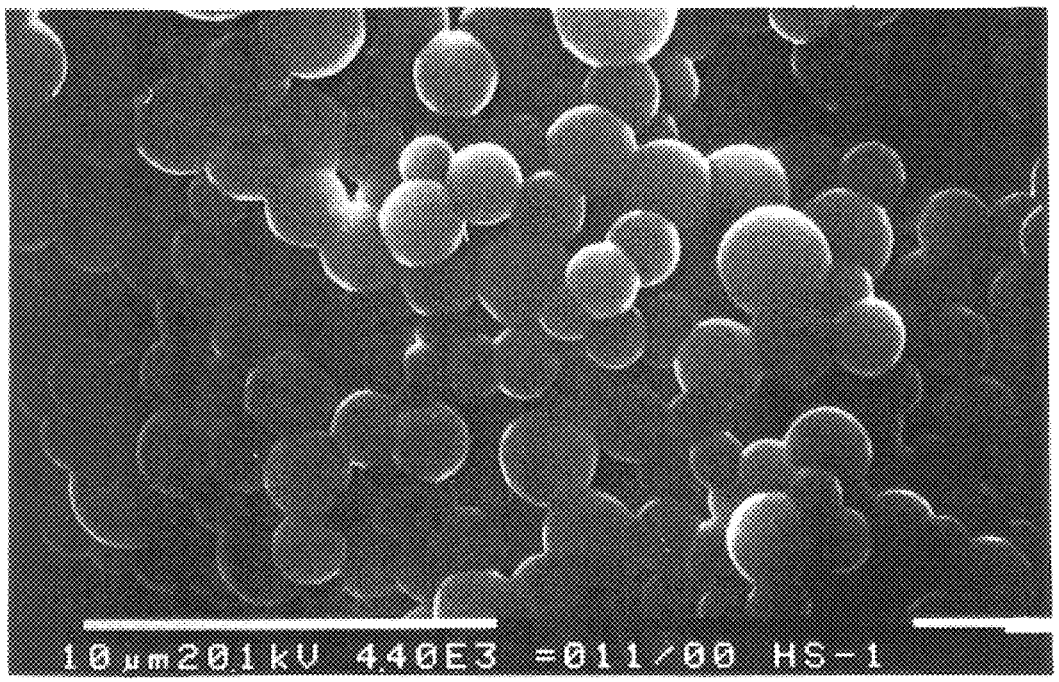
FIG. 13 shows the morphology of the TS1 (top) and as co-aggregates with human platelets (bottom) by scanning electron microscopy.
Figure 13B:
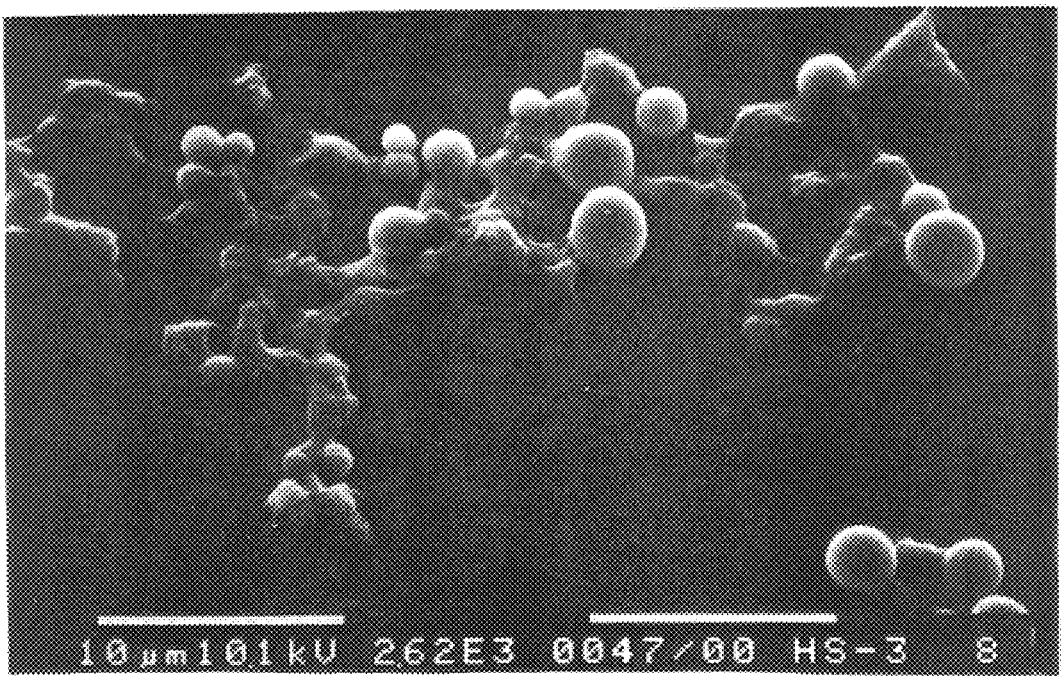

FIG. 13 shows the morphology of the TS1 (top) and as co-aggregates with human platelets (bottom) by scanning electron microscopy. The co-aggregates were produced by adding ADP (20 uM, final concentration) to a mixture of human platelets (100,000/uL) and TS1 (50,000/uL).

Figure 14A:
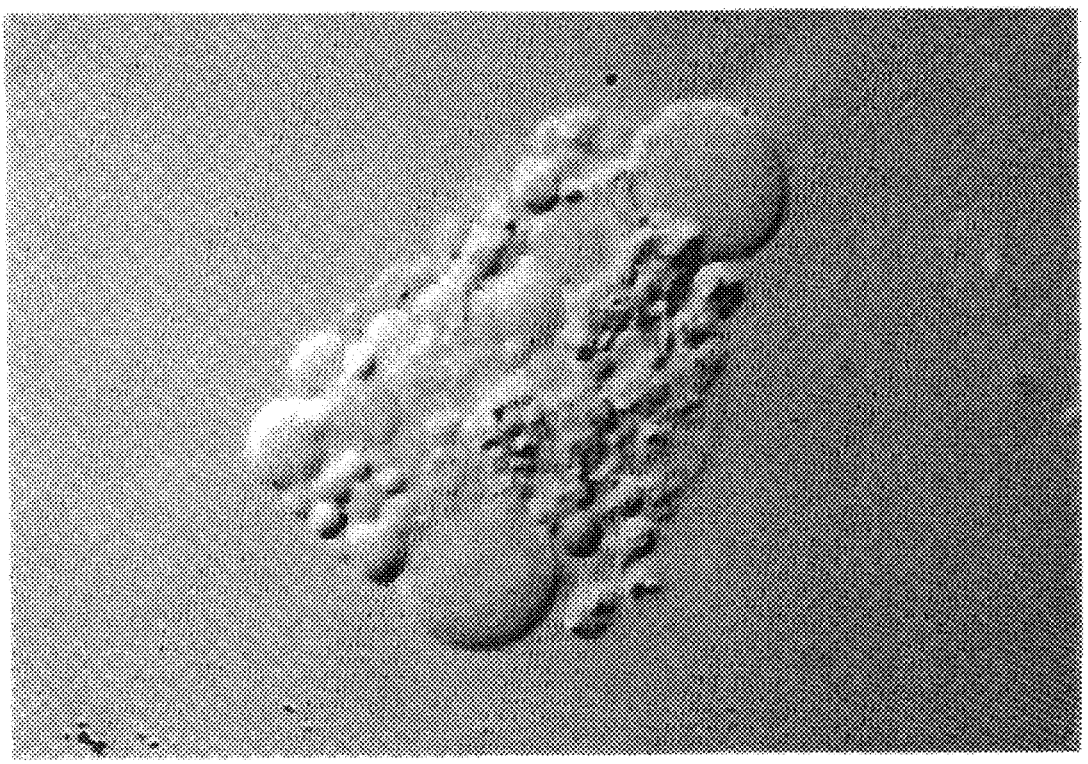
FIG. 14A shows phase contrast light microscopy of co-aggregates between TS1 and activated human platelets.
Figure 14B:
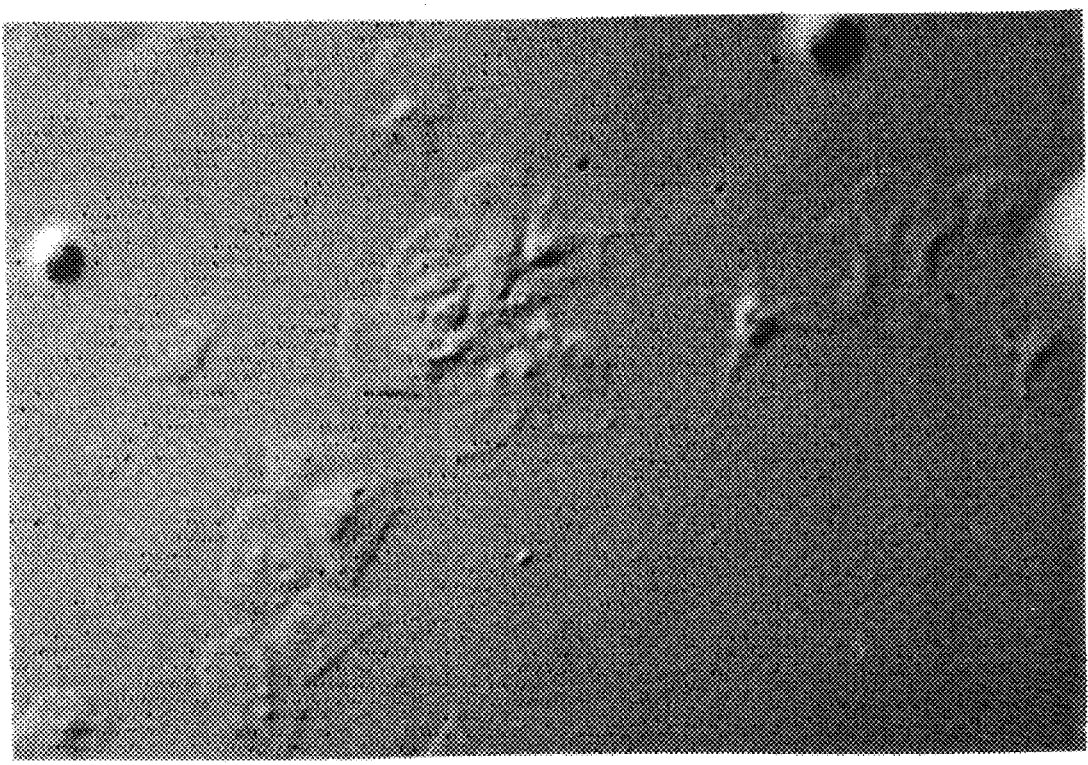
FIG. 14B shows the lack of interaction between CS and platelets after activation by ADP.

FIG. 14A shows under phase contrast light microscopy the co-aggregates between TS1 and activated human platelets (activated by ADP in a mixture of 50:100×$10^3$/ul of TS :platelets, respectively). However, mixtures of platelets with CS showed only pure platelet aggregates after activation by ADP, without inclusion of any CS in the aggregates. FIG. 14B showed the lack of interaction between CS and platelets after activation by ADP.

TS Structure

Figure 15A:
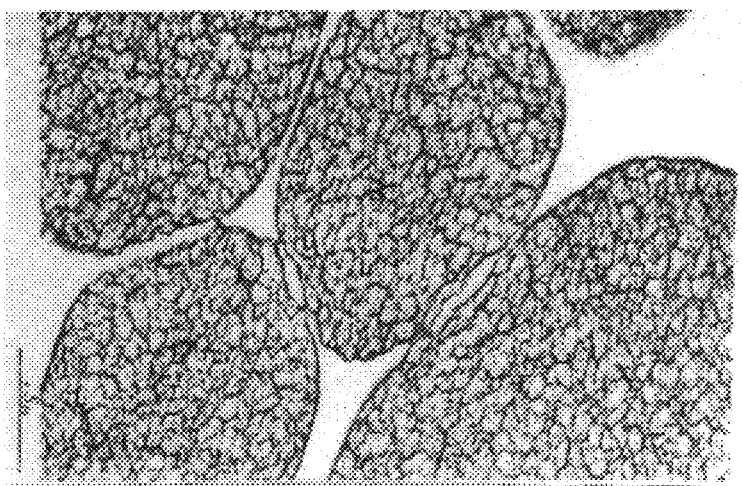
FIG. 15A–E shows transmission electron microscopy of the internal structure of spheres.
Figure 15B:
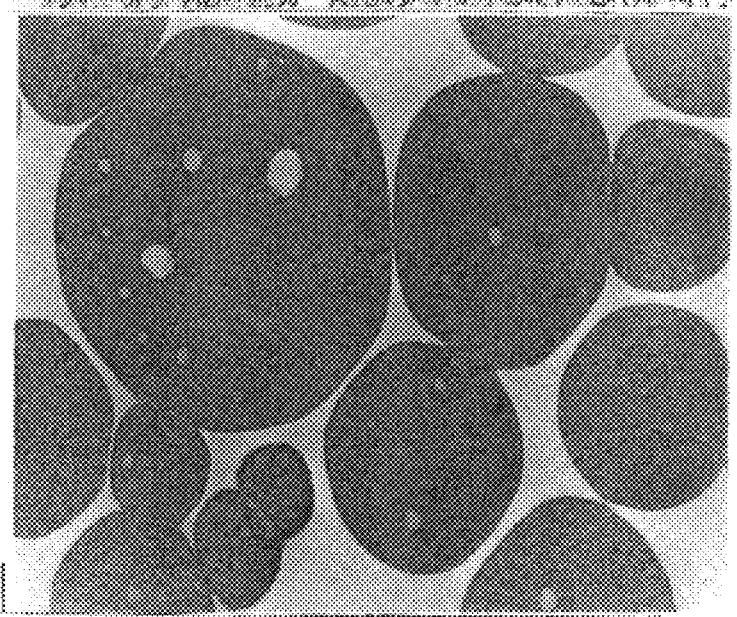
Figure 15C:
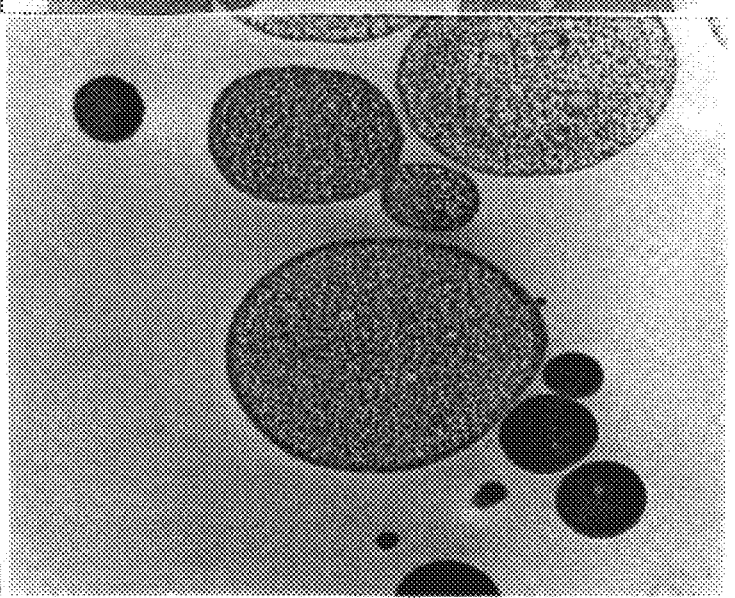
Figure 15D:
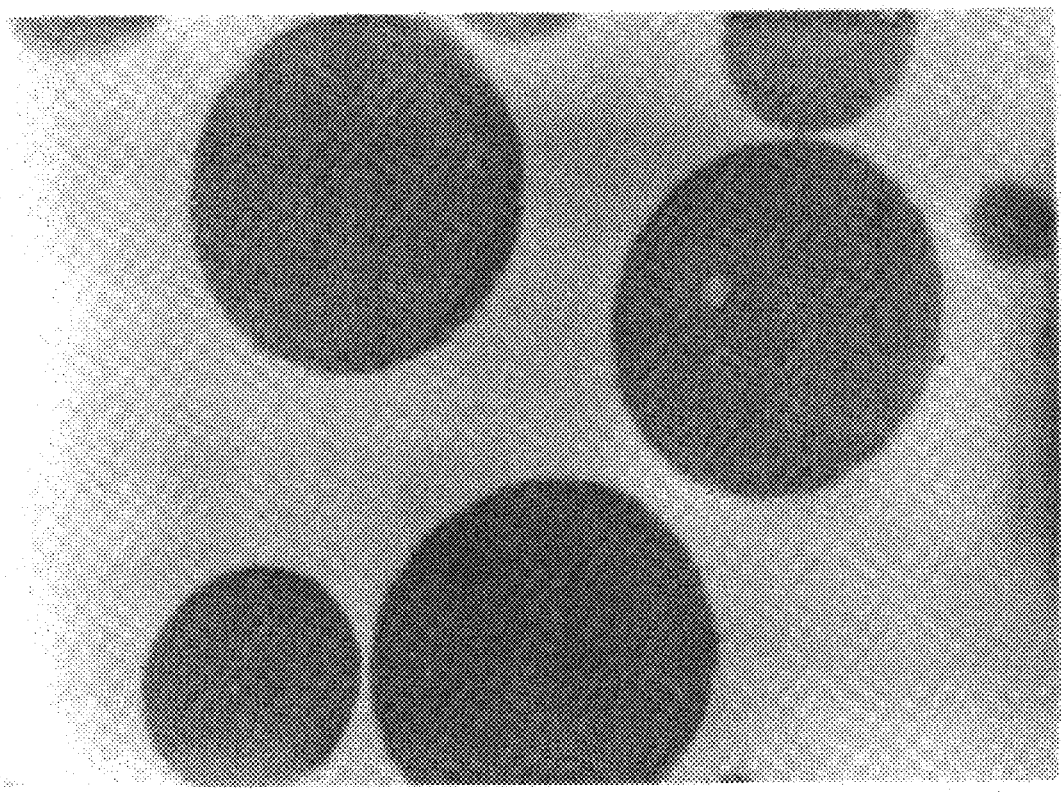
Figure 15E:
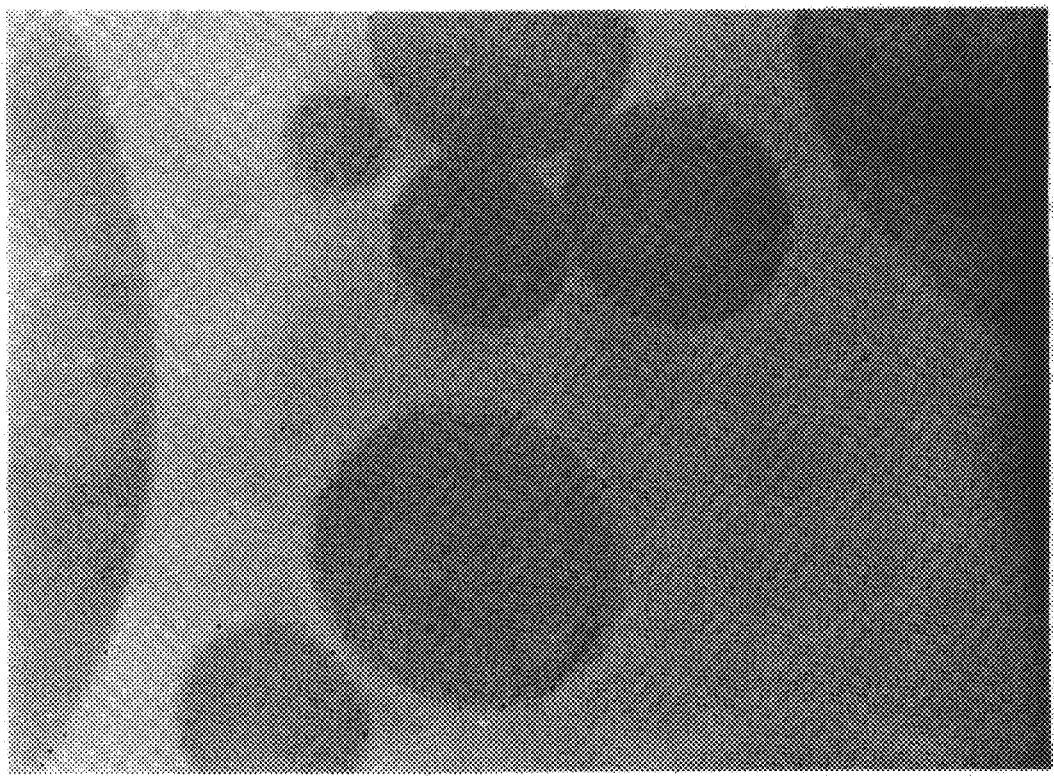
Figure 16A:
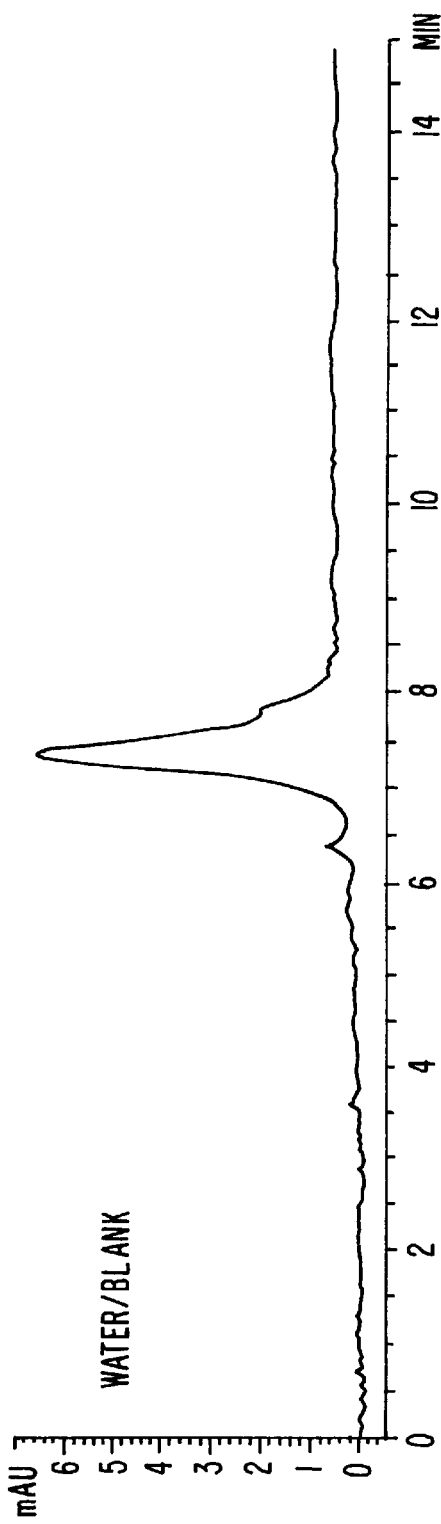
FIG. 16 shows a chromatogram of reactive aldehyde groups on CS and TS3.
Figure 16B:
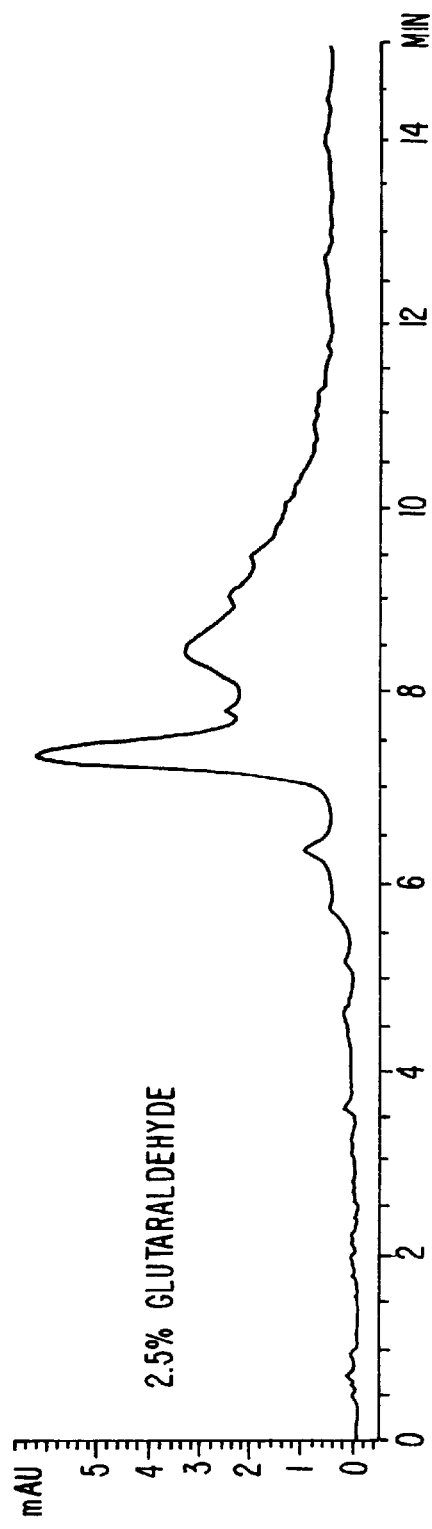
Figure 16C:
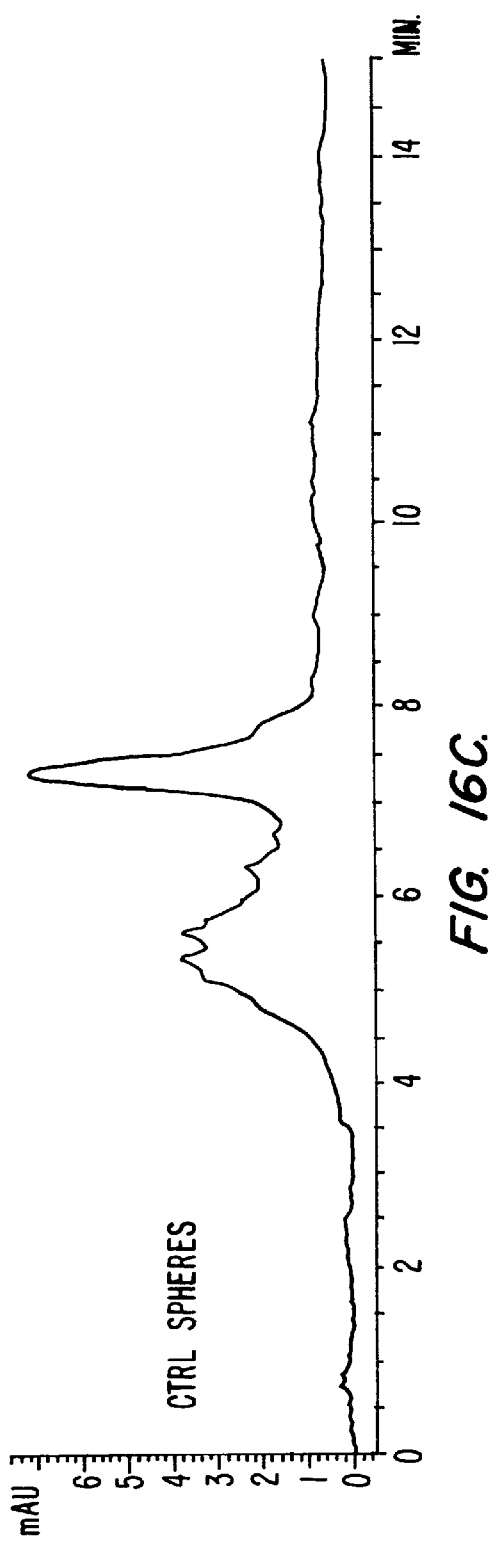
Figure 16D:
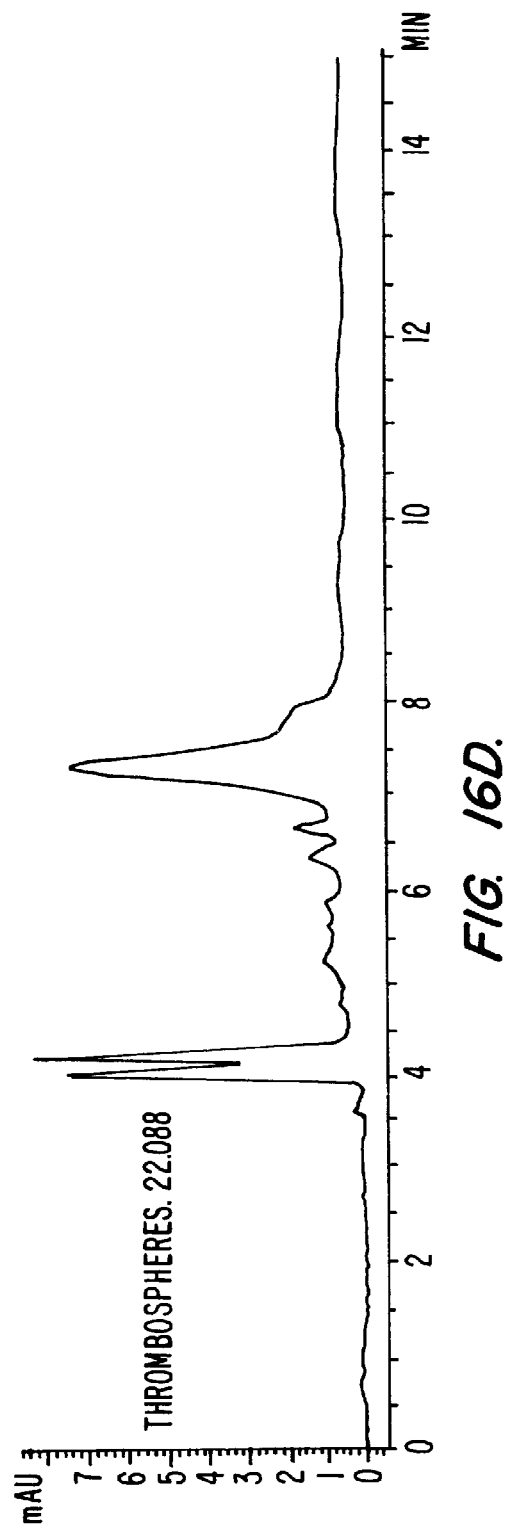

The internal structure of the spheres was studied with the transmission electron microscope. FIG. 15A shows a cross section of a CS (not stained) which reveals a sponge-like internal structure with fenestrations on the surface leading to the internal matrixes. FIG. 15B is a microscopy picture of a cross section of TS1 (Lot K9401) which was not stained. It revealed a dense material filling the internal "empty spaces" of the spheres as well as "blocking" the fenestrations on the surface as seen in the CS. Upon staining with a uranyl acetate/lead citrate solution, a rim of densely labeled material measuring about 0.15 micron thick surround the sphere could be observed (FIG. 15C). Similarly dense material was seen to have packed the air-pockets inside the spheres. FIG. 15E shows the cross section of TS1 (Lot K9401) first labeled with sheep anti-human fibrinogen IgG which was then tagged with protein A-gold ligands (arrows). This showed that the dense material surround the spheres was human fibrinogen. Colloidal gold was not present on TS1 (Lot K9401) treated with buffer and protein A-gold in the absence of anti-human fibrinogen IgG (FIG. 15D) or on CS treated with either anti-human fibrinogen IgG or buffer (data not shown.)

Release Assays

Table 13 lists some of the release assays and other characteristics of the preparations. TS1 (Lot K9401) had the highest FPA concentration (both FPA/mL suspension of the reconstituted product, and FPA/$10^9$ TS.) The FPA concentrations of TS2 (both Lot 22.026 and Lot 22.029) were approaching the zero baseline value. Although the FPA/mL was different for TS3 (Lot 22.033 and 22.038), when the FPA concentration was corrected for TS concentration (FPA/$10^9$TS), the values were comparable. The relatively high alcohol content of Lot 22.026 was probably due to a shortened cycle of lyophilization. The presence of excipients in Lot 22.026, 22.029, 22.033 and 22.038 appears to have greatly reduced reconstitution time. Significantly, the concentration of large particles was greatly reduced in the filtered lots compared to Lot K9401 or CS.

FIG. 16 shows the chromatogram after interaction of CS and TS3 (Lot 22.038) with DNP, which indicated the presence of reactive aldehyde groups with both kinds of spheres.

The foregoing is offered primarily for purposes of illustration. It will be readily apparent to those skilled in the art that the materials, proportions, methods of preparation and formulation and other parameters of the various systems described herein may be further modified or substituted in various ways without departing from the spirit and scope of the invention.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

What is claimed is:

1. A suspension of fibrinogen-coated cross-linked protein microspheres useful for reducing bleeding time in an animal with a platelet deficiency or dysfunction, said suspension comprising microspheres of cross-linked protein, said microspheres being monodisperse in said suspension, having internal structure with fenestrations on the surface leading to internal matrices, and having a size range of primarily from abotut 100 to about 5000 nanometers diameter, said microspheres further comprising on their surface fibrinogen, wherein at least a portion of said fibrinogen is covalently bound to the protein, and wherein said suspension is substantially free of microspheres and microsphere aggregates having a diameter of more than 7 micrometers.

TABLE 13

RELEASE AND OTHER ASSAYS FOR CS, TS1, TS3

| Assays | CS | K9401 | 22.033 | 22.038 |
|---|---|---|---|---|
| 1. FPA (ng/ml) | 0 | 508 | 114 | 223 |
| 2. FPA (ng/$10^9$ TS) | 0 | 203 | 71 | 74 |
| 3. Mean Diameter (micron, by Coulter) | 1.15 | 1.06 | 1.03 | 1.04 |
| 4. Concentration (10(9) TS/ml after reconstitution) | 2.8 | 2.49 | 1.6 | 3.0 |
| 5. Large Particles (>7 micron) × 10(6)/ml | 9 | 10 | 0.3 | 0.5 |
| 6. Free Protein in Supernatant (mg/ml) | 0.71 | 1.87 | 2.27 | 2.60 |
| 7. Glutaraldehyde in supernatant | 0.006% | 0.007% | 0.009% | 0.008% |
| 8. Ethanol in Supernatant | n.d. | 0.013% | 0.063% | n.d. |
| 9. pH | 6.50 | 6.17 | 6.17 | 6.16 |
| 10. Reconstitution Time | >60 min | >60 min | 5 min | 5 min |
| 11. Color/Appearance (lyophilized product) | White to yellow cake | White to yellow cake | White to yellow cake | White to yellow cake |
| 12. Moisture (by Carl Fisher) | n.d. | n.d. | 0.35% | n.d. |
| 13. Color/Appearance (reconstituted product) | Opaque light yellow suspension | Opaque light yellow suspension | Opaque light yellow suspension | Opaque light yellow suspension |
| 14. Osmolarity (mOsm/ml) | n.d. | 348 | 319 | n.d. |
| 15. Sterility (14 days) | Sterile | Sterile | Sterile | Sterile |
| 16. USP Pyrogen Test (rabbit) | Negative | Negative | Negative | Negative |

Stability of TS During Storage at 4° C.

Figure 17A:
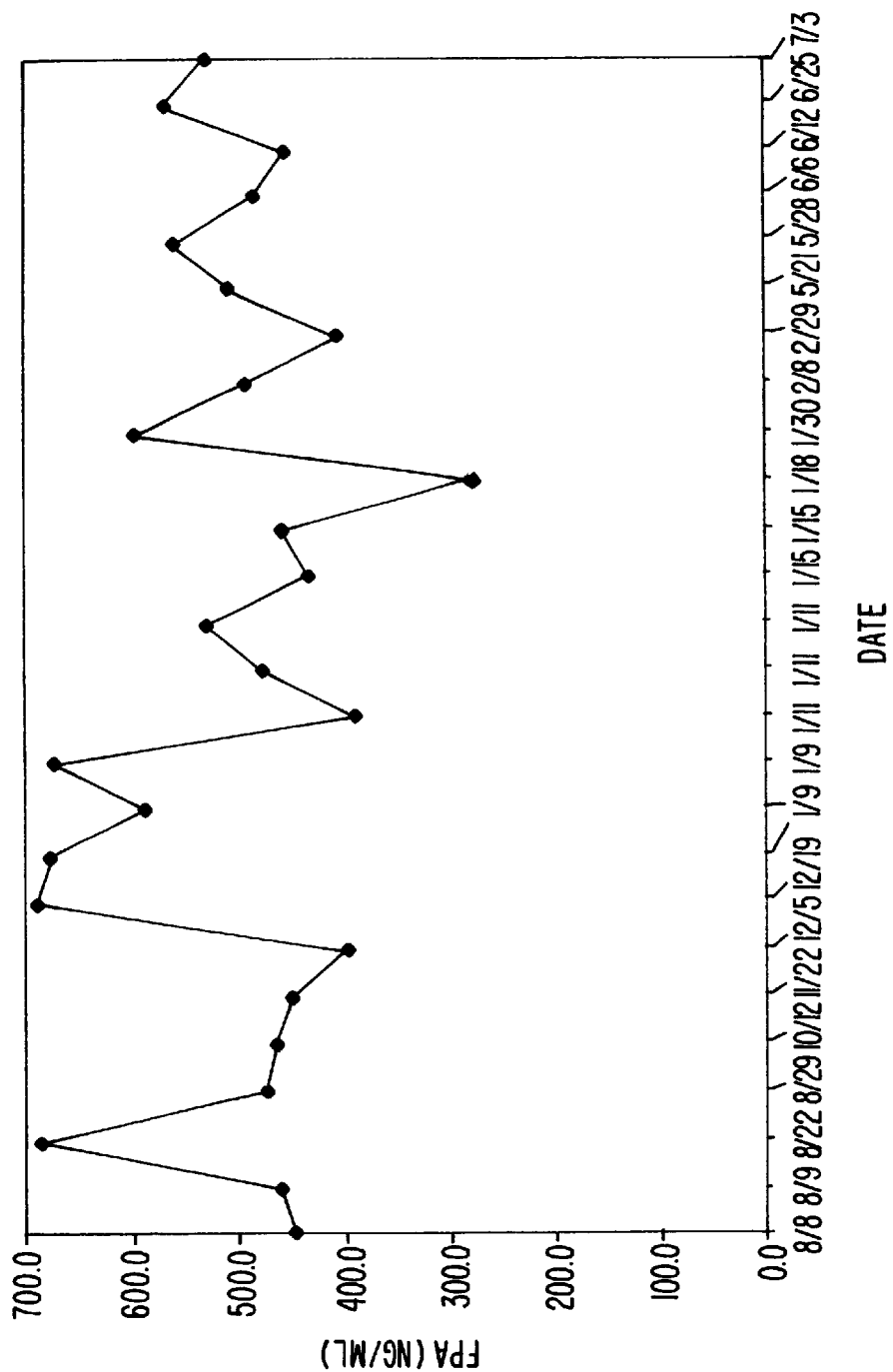
FIG. 17A shows the overall concentration of FPA/mL over a period of a year.
Figure 17B:
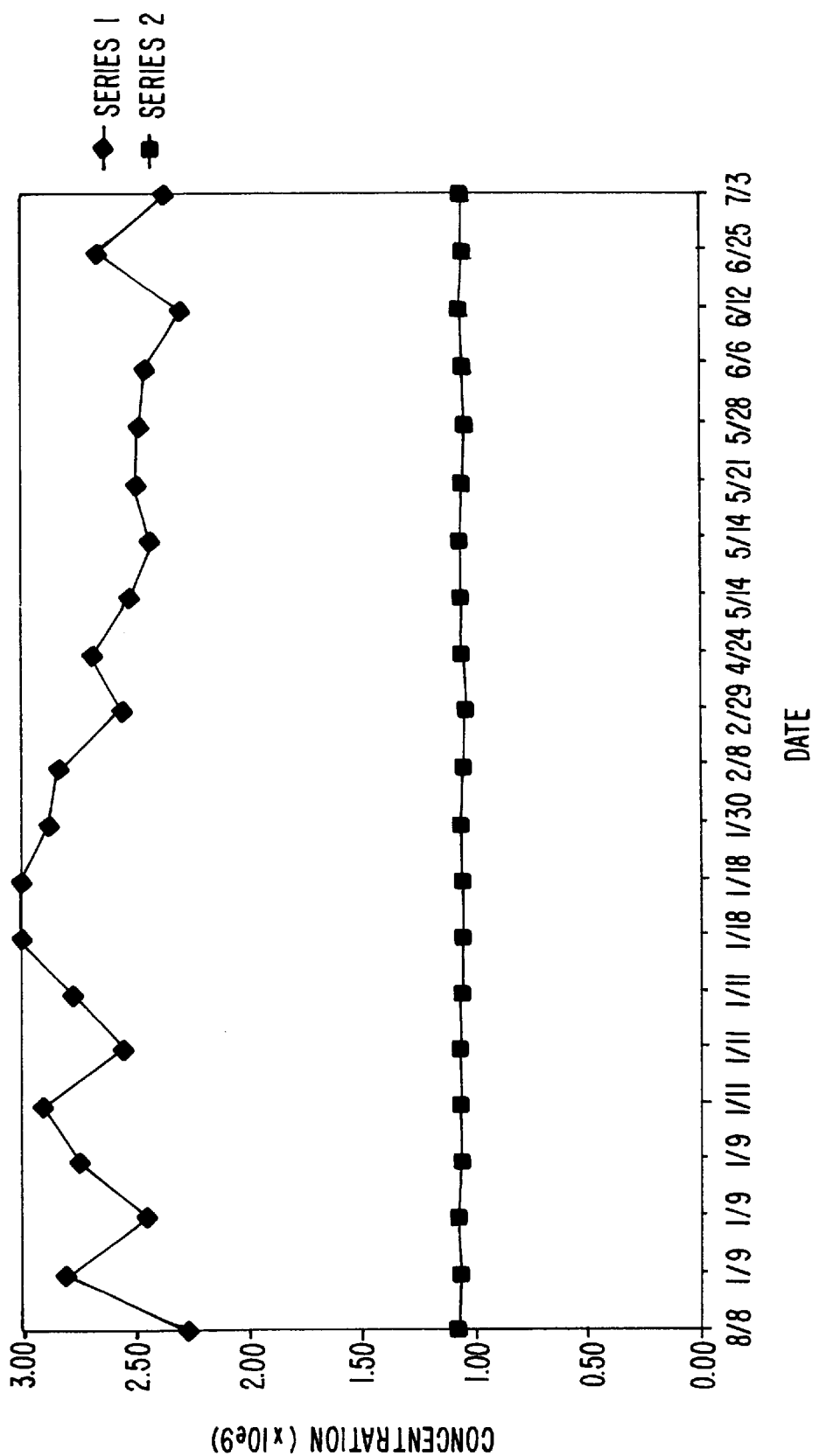
FIG. 17B shows the concentration of spheres and their mean diameter.
Figure 18A:
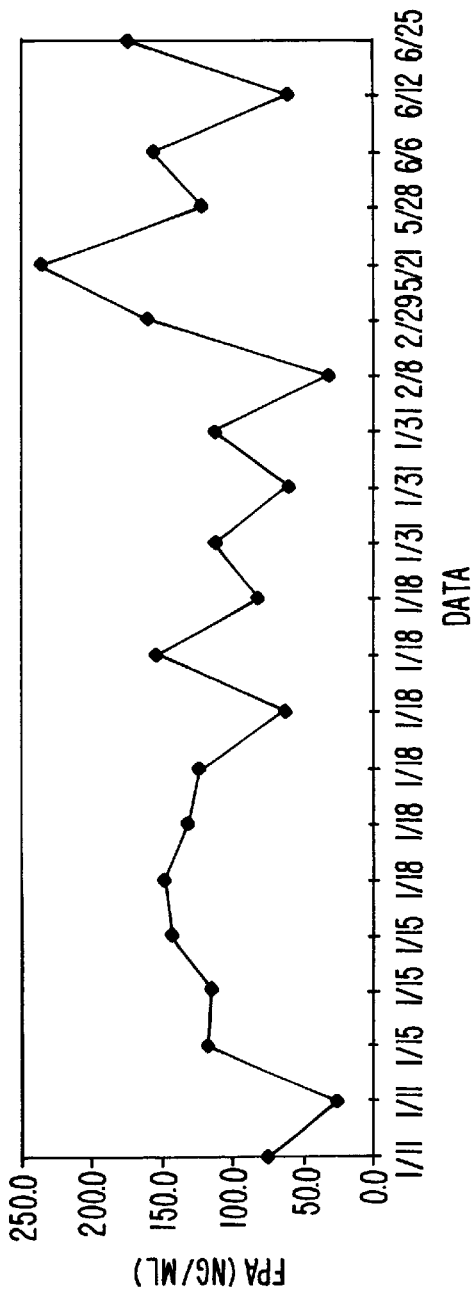
FIG. 18 shows that the FPA content of TS3 was stable for at least 6 months.
Figure 18B:
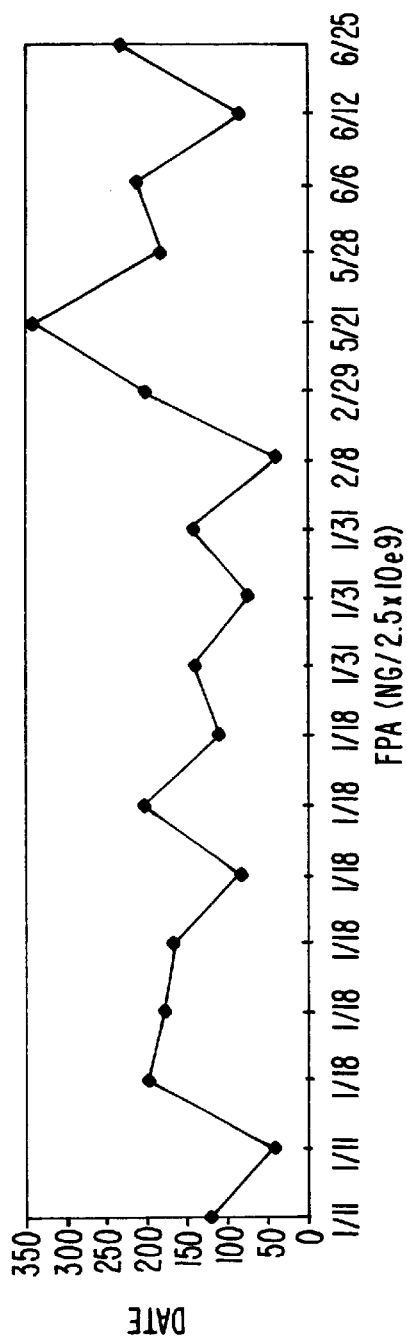

The FPA content of TS1 appears to fluctuate between 300 to 700 ng/mL, it probably represent the variation in assay technique because over the period of almost a year, the overall concentration of FPA/mL remained steady (FIG. 17A). The concentration of spheres and their mean diameter as measured by the Coulter Multisizer also remained constant (FIG. 17B). The FPA content of TS3 (Lot 22.033) (ng/mL and ng/2.5×$10^9$ TS) which was shown (FIG. 18) to be stable for the period studied (6 months).

2. The suspension of claim 1, wherein said microspheres comprise human serum albumin cross-linked by treatment with glutaraldehyde.

3. The suspension of claim 2, wherein the fibrinogen is recombinant or naturally occuring.

4. The suspension of claim 2, wherein said microspheres have a sponge-like internal structure with fenestrations on the surface leading to internal matrices.

5. The suspension of claim 4, wherein at least about 50% of the microspheres by number are between about 100 and about 500 nanometers in diameter, and at least about 10% are between about and 500 nm and about 1700 nm in diameter.

6. The suspension of claim 4, wherein at least about 90% of said microspheres are between about 100 and about 500 nanometers in diameter.

7. The suspension of claim 4, wherein said suspension comprises fewer than about $3\times10^6$ microspheres greater than 7 μm in diameter per $10^9$ microspheres.

8. The suspension of claim 2 further comprising an excipient.

9. A dry composition produced by lyophilizing the suspension of claim 8 and characterized by having a reconstitution time of less than about 10 minutes.

10. The suspension of claim 5, wherein said microspheres comprise at least about $4\times10^{12}$ molecules of fibrinogen per $10^9$ microspheres.

11. A method of making fibrinogen-coated microspheres useful for reducing bleeding time in an animal with a platelet deficiency or disfunction, comprising the steps of: adding a desolvating agent to an aqueous mixture of a protein and a surfactant, whereupon a turbid mixture comprising substantially monodisperse protein microspheres results; adding a first crosslinking agent to the turbid mixture; removing large microspheres and microsphere aggregates from the mixture; adding a second cross-linking agent, which may be the same as the first cross-linking agent; and adding fibrinogen.

12. The method of claim 11, wherein the protein is human serum albumin, the desolvating agent is ethanol, the surfactant is sodium tetradecyl sulfate, the first cross-linking agent is glutaraldehyde, the second cross-linking agent is glutaraldehyde, and said large microspheres and microsphere aggregates are removed by filtration or centrifugation.

13. A suspension of microspheres made according to claim 11.

14. A method of making fibrinogen-coated microspheres useful for reducing bleeding time in an animal with a platelet deficiency or disfunction, comprising the steps of: adding a desolvating agent to an aqueous mixture of a protein and a surfactant, whereupon a turbid mixture comprising substantially monodisperse protein microspheres results; adding a crosslinking agent to the turbid mixture; adding fibrinogen to the mixture whereupon the particles are coated with the fibrinogen; and removing large particles and aggregates from the mixture.

15. The method of claim 14, wherein the protein is human serum albumin, the desolvating agent is ethanol, the surfactant is sodium tetradecyl sulfate, the cross-linking agent is glutaraldehyde, and said large microspheres and microsphere aggregates are removed by centrifugation.

16. A suspension of microspheres made according to claim 14.

17. A method of reducing bleeding time in an animal comprising administering a therapeutically effective amount of the suspension of claim 1.

18. A method of reducing bleeding time in an animal comprising administering a therapeutically effective amount of the suspension of claim 13.

19. The method of claim 18, wherein the animal is a human.

20. The method of claim 18, wherein said administering comprises administering at least two doses of said suspension, wherein the second dose is administered within about 24 hours after administering the first dose.

21. An aggregate-free suspension of microspheres capable of reducing bleeding time in an animal, when administered according to the method of claim 20.

\* \* \* \* \*